United States Patent
Baty et al.

(10) Patent No.: US 10,287,360 B2
(45) Date of Patent: May 14, 2019

(54) ANTI-EGFR CONFORMATIONAL SINGLE DOMAIN ANTIBODIES AND USES THEREOF

(71) Applicants: INSERM (INSTITUT NATIONAL DE LA SANTÉ ET DE LA RECHERCHE MÉDICALE), Paris (FR); UNIVERSITÉ D'AIX MARSEILLE, Marseilles (FR); CENTRE NATIONAL DE LA RECHERCHE SCIENTIFIQUE (CNRS), Paris (FR); CISBIO BIOASSAYS, Codolet (FR); INSTITUT JEAN PAOLI & IRENE CALMETTES, Marseilles (FR)

(72) Inventors: Daniel Baty, Marseilles (FR); Patrick Chames, Marseilles (FR); Damien Nevoltris, Marseilles (FR); Gérard Mathis, Codolet (FR)

(73) Assignees: INSERM (Institut National de la Santé et de la Recherche Médicale, Paris (FR); Université d' Aix-Marseille, Marseilles (FR); Centre National de la Recherche Scientifique (CNRS), Paris (FR); CISBIO Bioassays, Codolet (FR); Institut Jean Paoli & Irene Calmettes, Marseilles (FR)

(*) Notice: Subject to any disclaimer, the term of this patent is extended or adjusted under 35 U.S.C. 154(b) by 0 days.

(21) Appl. No.: 15/313,114

(22) PCT Filed: May 22, 2015

(86) PCT No.: PCT/EP2015/061419
§ 371 (c)(1),
(2) Date: Nov. 22, 2016

(87) PCT Pub. No.: WO2015/177349
PCT Pub. Date: Nov. 26, 2015

(65) Prior Publication Data
US 2017/0190787 A1 Jul. 6, 2017

(30) Foreign Application Priority Data

May 23, 2014 (EP) ..................... 14305766

(51) Int. Cl.
*C07K 16/32* (2006.01)
*G01N 33/74* (2006.01)
*C07K 16/28* (2006.01)
*G01N 33/574* (2006.01)
*A61K 39/00* (2006.01)

(52) U.S. Cl.
CPC .......... *C07K 16/32* (2013.01); *C07K 16/2863* (2013.01); *G01N 33/5748* (2013.01); *G01N 33/74* (2013.01); *A61K 2039/507* (2013.01); *C07K 2317/22* (2013.01); *C07K 2317/24* (2013.01); *C07K 2317/30* (2013.01); *C07K 2317/31* (2013.01); *C07K 2317/33* (2013.01); *C07K 2317/569* (2013.01); *C07K 2317/75* (2013.01); *C07K 2317/92* (2013.01); *G01N 2333/71* (2013.01)

(58) Field of Classification Search
CPC .... C07K 16/32; C07K 16/2863; G01N 33/74; G01N 33/5748
USPC ...................................... 424/133.1
See application file for complete search history.

(56) References Cited

PUBLICATIONS

Ward et al. (Nature 341:544-546 (1989)).*
Kruwel et al. Sci. Rep. 6, 21834; doi: 10.1038/srep21834 (2016).*
Neveltris et al. ASCNano 9(2): 1388-1399 (2015).*
Schmitz et al., "Structural Evaluation of EGFR Inhibition Mechanisms for Nanobodies/VHH Domains", Structure, Jun. 20, 2013, pp. 1214-1224, vol. 21, No. 7, Current Biology Ltd., Philadelphia, PA.
Roovers et al., "A bioparatopic anti-EGFR nanobody efficiently inhibits solid tumour growth", International Journal of Cancer, Oct. 15, 2011, pp. 2013-2024, vol. 129, No. 8.
Kelton et al., "Anti-EGFR biparatopic-SEED antibody has enhanced combination-activity in a single molecule", Archives of Biochemistry and Biophysics, Oct. 1, 2012, pp. 219-225, vol. 526, No. 2.
Shiqing et al., "Structural basis for inhibition of the epidermal growth factor receptor by cetuximab", Cancer Cell, Apr. 1, 2005, pp. 301-311, vol. 7, No. 4, Cell Press, US.
Schmiedel et al., "Matuzumab Binding to EGFR Prevents the Conformational Rearrangement Required for Dimerization", Cancer Cell, Apr. 1, 2008, pp. 301-311, vol. 7, No. 5.
Zarschler et al., "Diagnostic nanoparticle targeting of the EGF-receptor in complex biological conditions using single-domain antibodies", Nanoscale, Jan. 1, 2014, vol. 6, No. 11.

* cited by examiner

*Primary Examiner* — Lynn A Bristol
(74) *Attorney, Agent, or Firm* — W & C IP

(57) ABSTRACT

The present invention relates to anti-Epidermal Growth Factor Receptor (EGFR) conformational single domain antibodies and uses thereof in particular in the therapeutic and diagnostic field.

13 Claims, 13 Drawing Sheets

Figure 1B:
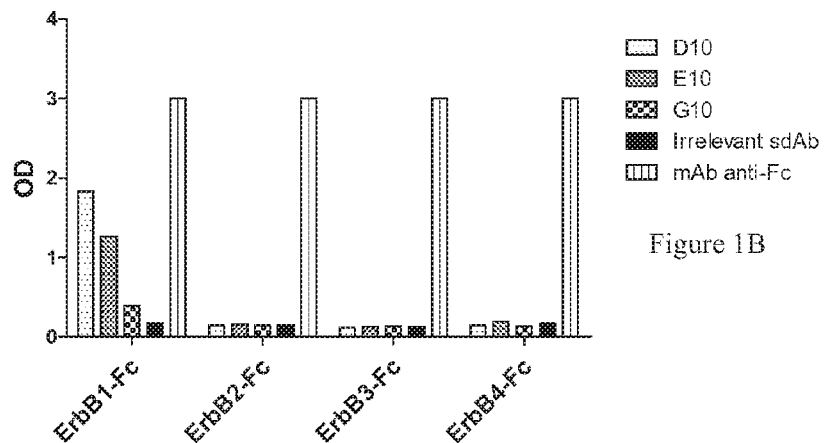

Specification includes a Sequence Listing.

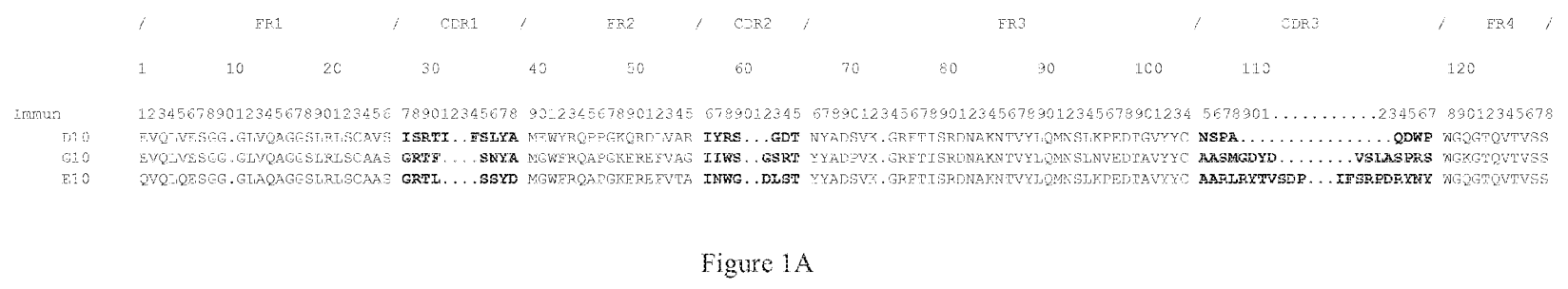

```
        /      FR1         /    CDR1   /     FR2         /   CDR2  /                      FR3                          /    CDR3      /    FR4   /
        1234567890123456  7890123456  78 9012345678901234 5 6789012345  6789012345678901234567890123456789 01234 56789 01.........2345 67 89012345678
        1              10        20          30         40          50        60         70        80        90       100         110         120
Immun   EVQ.VE.SGG.GLVQAGGSLRLSCAVS  ISRTI..FSLYA MTWVRQPEGKQRD-VAR IYRS...GDT NYADSVK.GRFTTSRDNAKNTVYLQMNSLKPEDTGVYYC  NSPA...........2345 67 QDWP WGQGTQVTVSS
D10     EVQLVESGG.GLVQAGGSLRLSCAAS  GRTF....SNYA MGWFRQAPGKEREFVAG LIWS...GSRP YYADPVK.GRFTISRDNAKNTVYLQMNSLNVEDTAVYYC  AASMGDYD.......VSLASPRS WGKGTQVTVSS
G10     EVQLVESGG.GLVQAGGSLRLSCAAS  GRTF....SNYA MGWFRQAPGKEREFVAG LIWS...GSRP YYADSVK.GRFTISRDNAKNTVYLQMNSLNVEDTAVYYC  AASMGDYD.......VSLASPRS WGKGTQVTVSS
E10     QVQ.QESGG.GLAQAGGSLRLSCAAS  GRTL....SSYD MGWFRQATGKEREFVTA INWG...DLST YYADSVK.GRFTLSRDNAKNTVYLQMNSLKPEDTAVYYC  AAFLRVTVSDP...IFSRPDVNY WGQGTQVTVSS
```

Figure 1A

A.

B.

SEQUENCE LISTING

<160> NUMBER OF SEQ ID NOS: 15

<210> SEQ ID NO 1
<211> LENGTH: 10
<212> TYPE: PRT
<213> ORGANISM: Artificial
<220> FEATURE:
<223> OTHER INFORMATION: Synthetic D10 CDR1

<400> SEQUENCE: 1

Ile Ser Arg Thr Ile Phe Ser Leu Tyr Ala
1               5                   10

<210> SEQ ID NO 2
<211> LENGTH: 7

```
<212> TYPE: PRT
<213> ORGANISM: Artificial
<220> FEATURE:
<223> OTHER INFORMATION: Synthetic D10 CDR2

<400> SEQUENCE: 2

Ile Tyr Arg Ser Gly Asp Thr
1               5

<210> SEQ ID NO 3
<211> LENGTH: 8
<212> TYPE: PRT
<213> ORGANISM: Artificial
<220> FEATURE:
<223> OTHER INFORMATION: Synthetic D10 CDR3

<400> SEQUENCE: 3

Asn Ser Pro Ala Gln Asp Trp Pro
1               5

<210> SEQ ID NO 4
<211> LENGTH: 116
<212> TYPE: PRT
<213> ORGANISM: Artificial
<220> FEATURE:
<223> OTHER INFORMATION: Synthetic D10

<400> SEQUENCE: 4

Glu Val Gln Leu Val Glu Ser Gly Gly Gly Leu Val Gln Ala Gly Gly
1               5                   10                  15

Ser Leu Arg Leu Ser Cys Ala Val Ser Ile Ser Arg Thr Ile Phe Ser
            20                  25                  30

Leu Tyr Ala Met Glu Trp Tyr Arg Gln Pro Pro Gly Lys Gln Arg Asp
        35                  40                  45

Leu Val Ala Arg Ile Tyr Arg Ser Gly Asp Thr Asn Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Gly Val Tyr Tyr
                85                  90                  95

Cys Asn Ser Pro Ala Gln Asp Trp Pro Trp Gly Gln Gly Thr Gln Val
            100                 105                 110

Thr Val Ser Ser
        115

<210> SEQ ID NO 5
<211> LENGTH: 8
<212> TYPE: PRT
<213> ORGANISM: Artificial
<220> FEATURE:
<223> OTHER INFORMATION: Synthetic G10 CDR1

<400> SEQUENCE: 5

Gly Arg Thr Phe Ser Asn Tyr Ala
1               5

<210> SEQ ID NO 6
<211> LENGTH: 8
<212> TYPE: PRT
<213> ORGANISM: Artificial
<220> FEATURE:
<223> OTHER INFORMATION: Synthetic G10 CDR2

<400> SEQUENCE: 6
```

```
Ile Ile Trp Ser Gly Ser Arg Thr
1               5

<210> SEQ ID NO 7
<211> LENGTH: 16
<212> TYPE: PRT
<213> ORGANISM: Artificial
<220> FEATURE:
<223> OTHER INFORMATION: Synthetic G10 CDR3

<400> SEQUENCE: 7

Ala Ala Ser Met Gly Asp Tyr Asp Val Ser Leu Ala Ser Pro Arg Ser
1               5                   10                  15

<210> SEQ ID NO 8
<211> LENGTH: 123
<212> TYPE: PRT
<213> ORGANISM: Artificial
<220> FEATURE:
<223> OTHER INFORMATION: Synthetic G10

<400> SEQUENCE: 8

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
                20                  25                  30

Ala Met Gly Trp Phe Arg Gln Ala Pro Gly Lys Glu Arg Glu Phe Val
            35                  40                  45

Ala Gly Ile Ile Trp Ser Gly Ser Arg Thr Tyr Tyr Ala Asp Pro Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Asn Val Glu Asp Thr Ala Val Tyr Tyr Cys
                85                  90                  95

Ala Ala Ser Met Gly Asp Tyr Asp Val Ser Leu Ala Ser Pro Arg Ser
                100                 105                 110

Trp Gly Lys Gly Thr Gln Val Thr Val Ser Ser
            115                 120

<210> SEQ ID NO 9
<211> LENGTH: 8
<212> TYPE: PRT
<213> ORGANISM: Artificial
<220> FEATURE:
<223> OTHER INFORMATION: Synthetic E10 CDR1

<400> SEQUENCE: 9

Gly Arg Thr Leu Ser Ser Tyr Asp
1               5

<210> SEQ ID NO 10
<211> LENGTH: 8
<212> TYPE: PRT
<213> ORGANISM: Artificial
<220> FEATURE:
<223> OTHER INFORMATION: Synthetic E10 CDR2

<400> SEQUENCE: 10

Ile Asn Trp Gly Asp Leu Ser Thr
1               5

<210> SEQ ID NO 11
```

```
<211> LENGTH: 21
<212> TYPE: PRT
<213> ORGANISM: Artificial
<220> FEATURE:
<223> OTHER INFORMATION: Synthetic E10 CDR3

<400> SEQUENCE: 11

Ala Ala Arg Leu Arg Tyr Thr Val Ser Asp Pro Ile Phe Ser Arg Pro
1               5                   10                  15

Asp Arg Tyr Asn Tyr
            20

<210> SEQ ID NO 12
<211> LENGTH: 128
<212> TYPE: PRT
<213> ORGANISM: Artificial
<220> FEATURE:
<223> OTHER INFORMATION: Synthetic E10

<400> SEQUENCE: 12

Gln Val Gln Leu Gln Glu Ser Gly Gly Gly Leu Ala Gln Ala Gly Gly
1               5                   10                  15

Ser Leu Arg Leu Ser Cys Ala Ala Ser Gly Arg Thr Leu Ser Ser Tyr
            20                  25                  30

Asp Met Gly Trp Phe Arg Gln Ala Pro Gly Lys Glu Arg Glu Phe Val
        35                  40                  45

Thr Ala Ile Asn Trp Gly Asp Leu Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Leu Arg Tyr Thr Val Ser Asp Pro Ile Phe Ser Arg Pro
            100                 105                 110

Asp Arg Tyr Asn Tyr Trp Gly Gln Gly Thr Gln Val Thr Val Ser Ser
        115                 120                 125

<210> SEQ ID NO 13
<211> LENGTH: 284
<212> TYPE: PRT
<213> ORGANISM: Artificial
<220> FEATURE:
<223> OTHER INFORMATION: Synthetic D2E

<400> SEQUENCE: 13

Glu Val Gln Leu Gln Glu Ser Gly Gly Gly Leu Val Gln Ala Gly Gly
1               5                   10                  15

Ser Leu Arg Leu Ser Cys Ala Val Ser Ile Ser Arg Thr Ile Phe Ser
            20                  25                  30

Leu Tyr Ala Met Glu Trp Tyr Arg Gln Pro Pro Gly Lys Gln Arg Asp
        35                  40                  45

Leu Val Ala Arg Ile Tyr Arg Ser Gly Asp Thr Asn Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Gly Val Tyr Tyr
                85                  90                  95

Cys Asn Ser Pro Ala Gln Asp Trp Pro Trp Gly Gln Gly Thr Gln Val
            100                 105                 110
```

```
Thr Val Ser Ser Ala Ala Ala Gly Gly Gly Ser Gly Gly Gly
            115                 120                 125

Ser Met Ala Gln Val Gln Leu Gln Glu Ser Gly Gly Leu Ala Gln
    130                 135                 140

Ala Gly Gly Ser Leu Arg Leu Ser Cys Ala Ala Ser Gly Arg Thr Leu
145                 150                 155                 160

Ser Ser Tyr Asp Met Gly Trp Phe Arg Gln Ala Pro Gly Lys Glu Arg
                165                 170                 175

Glu Phe Val Thr Ala Ile Asn Trp Gly Asp Leu Ser Thr Tyr Tyr Ala
            180                 185                 190

Asp Ser Val Lys Gly Arg Phe Thr Ile Ser Arg Asp Asn Ala Lys Asn
        195                 200                 205

Thr Val Tyr Leu Gln Met Asn Ser Leu Lys Pro Glu Asp Thr Ala Val
    210                 215                 220

Tyr Tyr Cys Ala Ala Arg Leu Arg Tyr Thr Val Ser Asp Pro Ile Phe
225                 230                 235                 240

Ser Arg Pro Asp Arg Tyr Asn Tyr Trp Gly Gln Gly Thr Gln Val Thr
                245                 250                 255

Val Ser Ser Ala Ala Ala Glu Gln Lys Leu Ile Ser Glu Glu Asp Leu
            260                 265                 270

Asn Gly Ala Ala His His His His His His Gly Ser
    275                 280

<210> SEQ ID NO 14
<211> LENGTH: 294
<212> TYPE: PRT
<213> ORGANISM: Artificial
<220> FEATURE:
<223> OTHER INFORMATION: Synthetic D4E

<400> SEQUENCE: 14

Glu Val Gln Leu Gln Glu Ser Gly Gly Gly Leu Val Gln Ala Gly Gly
1               5                   10                  15

Ser Leu Arg Leu Ser Cys Ala Val Ser Ile Ser Arg Thr Ile Phe Ser
            20                  25                  30

Leu Tyr Ala Met Glu Trp Tyr Arg Gln Pro Pro Gly Lys Gln Arg Asp
        35                  40                  45

Leu Val Ala Arg Ile Tyr Arg Ser Gly Asp Thr Asn Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Gly Val Tyr Tyr
                85                  90                  95

Cys Asn Ser Pro Ala Gln Asp Trp Pro Trp Gly Gln Gly Thr Gln Val
            100                 105                 110

Thr Val Ser Ser Ala Ala Ala Gly Gly Gly Gly Ser Gly Gly Gly Gly
        115                 120                 125

Ser Gly Gly Gly Gly Ser Gly Gly Gly Gly Ser Met Ala Gln Val Gln
    130                 135                 140

Leu Gln Glu Ser Gly Gly Gly Leu Ala Gln Ala Gly Gly Ser Leu Arg
145                 150                 155                 160

Leu Ser Cys Ala Ala Ser Gly Arg Thr Leu Ser Ser Tyr Asp Met Gly
                165                 170                 175

Trp Phe Arg Gln Ala Pro Gly Lys Glu Arg Glu Phe Val Thr Ala Ile
            180                 185                 190
```

Asn Trp Gly Asp Leu Ser Thr Tyr Tyr Ala Asp Ser Val Lys Gly Arg
            195                 200                 205

Phe Thr Ile Ser Arg Asp Asn Ala Lys Asn Thr Val Tyr Leu Gln Met
    210                 215                 220

Asn Ser Leu Lys Pro Glu Asp Thr Ala Val Tyr Tyr Cys Ala Ala Arg
225                 230                 235                 240

Leu Arg Tyr Thr Val Ser Asp Pro Ile Phe Ser Arg Pro Asp Arg Tyr
            245                 250                 255

Asn Tyr Trp Gly Gln Gly Thr Gln Val Thr Val Ser Ser Ala Ala Ala
            260                 265                 270

Glu Gln Lys Leu Ile Ser Glu Glu Asp Leu Asn Gly Ala Ala His His
            275                 280                 285

His His His His Gly Ser
    290

<210> SEQ ID NO 15
<211> LENGTH: 304
<212> TYPE: PRT
<213> ORGANISM: Artificial
<220> FEATURE:
<223> OTHER INFORMATION: Synthetic D6E

<400> SEQUENCE: 15

Glu Val Gln Leu Gln Glu Ser Gly Gly Gly Leu Val Gln Ala Gly Gly
1               5                   10                  15

Ser Leu Arg Leu Ser Cys Ala Val Ser Ile Ser Arg Thr Ile Phe Ser
            20                  25                  30

Leu Tyr Ala Met Glu Trp Tyr Arg Gln Pro Pro Gly Lys Gln Arg Asp
            35                  40                  45

Leu Val Ala Arg Ile Tyr Arg Ser Gly Asp Thr Asn Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Gly Val Tyr Tyr
            85                  90                  95

Cys Asn Ser Pro Ala Gln Asp Trp Pro Trp Gly Gln Gly Thr Gln Val
            100                 105                 110

Thr Val Ser Ser Ala Ala Ala Gly Gly Gly Gly Ser Gly Gly Gly Gly
    115                 120                 125

Ser Gly Gly Gly Gly Ser Gly Gly Gly Gly Ser Gly Gly Gly Gly Ser
130                 135                 140

Gly Gly Gly Gly Ser Met Ala Gln Val Gln Leu Gln Glu Ser Gly Gly
145                 150                 155                 160

Gly Leu Ala Gln Ala Gly Gly Ser Leu Arg Leu Ser Cys Ala Ala Ser
            165                 170                 175

Gly Arg Thr Leu Ser Ser Tyr Asp Met Gly Trp Phe Arg Gln Ala Pro
            180                 185                 190

Gly Lys Glu Arg Glu Phe Val Thr Ala Ile Asn Trp Gly Asp Leu Ser
            195                 200                 205

Thr Tyr Tyr Ala Asp Ser Val Lys Gly Arg Phe Thr Ile Ser Arg Asp
    210                 215                 220

Asn Ala Lys Asn Thr Val Tyr Leu Gln Met Asn Ser Leu Lys Pro Glu
225                 230                 235                 240

Asp Thr Ala Val Tyr Tyr Cys Ala Ala Arg Leu Arg Tyr Thr Val Ser
            245                 250                 255

-continued

```
Asp Pro Ile Phe Ser Arg Pro Asp Arg Tyr Asn Tyr Trp Gly Gln Gly
            260                 265                 270

Thr Gln Val Thr Val Ser Ser Ala Ala Ala Glu Gln Lys Leu Ile Ser
        275                 280                 285

Glu Glu Asp Leu Asn Gly Ala Ala His His His His His His Gly Ser
    290                 295                 300
```

ANTI-EGFR CONFORMATIONAL SINGLE DOMAIN ANTIBODIES AND USES THEREOF

FIELD OF THE INVENTION

The present invention relates to anti-Epidermal Growth Factor Receptor (EGFR) conformational single domain antibodies and uses thereof in particular in the therapeutic and diagnostic field.

BACKGROUND OF THE INVENTION

The Epidermal Growth Factor Receptor (EGFR, also called ErbB1 or HER1) belongs to the family of single transmembrane domain receptors with tyrosine kinase activity driven by their intracellular domain. The EGFR family also includes ErbB2, ErbB3 and ErbB4 receptors. The extracellular domain of these receptors presents a ligand-binding site. The binding of a specific ligands induce the receptor activation, ultimately triggering signal transduction pathways involved in cell proliferation, migration, differentiation and survival (1). In addition to EGF itself, 11 different ligands have been shown to activate those receptors (including TGF-α, β-Cellulin and Neuregulins) (2). ErbB1 is activated by all ligands of this family except Neuregulins, specific for ErbB3 and ErbB4. These ligands bind to the extracellular domain of the receptor, inducing a major conformation change. This new conformation allows the formation of homodimers, or induce the formation of heterodimers with other members of the family (3). The structural basis for ligand-induced dimerization of ErbB extracellular regions is now well understood (4-9), and leads to an allosteric activation of the intracellular tyrosine kinase domain. However, although ligand binding and dimerization events seem connected, several studies have demonstrated that EGFR can also be found in the cell surface as non-activated dimers, also called predimers (10-13). The ligand-independent EGFR/ErbB2 dimer formation was shown to require the cytoplasmic domain of EGFR to be present on resting cells (14, 15). The relationship between extracellular region, transmembrane domains, intracellular juxtamemembrane domains and cytoplasmic tyrosine kinase of ErbB family receptors, plays a major role in the dimerization and activation events (16). Moreover, conformational changes during these activations appear to be key for the signal transduction. Because these inactive predimers are proposed to be primed for ligand binding and allow a fast and efficient signaling, they might represent a very relevant therapeutic target for small inhibitors. Unfortunately, despite the large amount of structural and functional data concerning the various states of EGFR, the conformation of its extracellular domain within predimers has never been captured by crystallography studies and remains largely unknown. Therefore, a precise monitoring of EGFR conformational changes appear crucial to thoroughly understand EGFR family signaling and help in the design of small-molecule drugs. Beside crystallography, other powerful methods such as nuclear magnetic resonance (17) or electron microscopy are increasingly used to solve high quality structures (18) but remain cumbersome and cannot be used on intact cells. Other methods are based on the use of mutant or fusion proteins (19, 20) but they also cannot be used on cells naturally expressing the wild type receptor. Molecular dynamics simulations (21) can provide essential insights but as any in silico prediction tools, it requires an experimental validation of the findings.

Recently, the use of non-conventional antibodies has emerged as a simple, new and sensitive approach to study protein conformation on living cells. Single domain antibodies (sdAbs, also called nanobodies) (22), correspond to the variable domains of a special class of antibodies naturally devoid of light chains found in Camelids. These small proteins (15 kDa) present several advantages (23) including a good thermal stability even without disulfide bond formation (24), a good solubility and high expression yield (25). Most importantly, sdAbs have a natural tendency to bind epitopes that are inaccessible to conventional antibodies (26), such as cleft and cavities. Consequently, they are often very sensitive to conformational changes of their target (27, 28). However, anti-Epidermal Growth Factor Receptor (EGFR) conformational single domain antibodies are still needed.

SUMMARY OF THE INVENTION

The present invention relates to anti-Epidermal Growth Factor Receptor (EGFR) conformational single domain antibodies and uses thereof in particular in the therapeutic and diagnostic field. In particular, the present invention is defined by the claims.

DETAILED DESCRIPTION OF THE INVENTION

The Epidermal Growth factor Receptor (EGFR) is a cell-surface receptor, with a single transmembrane domain and tyrosine kinase activity carried by the intracellular domain. This receptor is one of the four members of the ErbB family including ErbB2, ErbB3 and ErbB4. Ligand binding, like EGF binding, induces a conformational rearrangement of the receptor and induces a homo/heterodimerization essentially with ErbB family receptors that leads to the phosphorylation of the kinase domain, triggering a signaling cascade. EGFR can also form inactive dimers in a ligand-independent way through interactions between the cytoplasmic domains. In the present application, the inventors describe the successful selection and the characterization of anti-Epidermal Growth Factor Receptor (EGFR) conformational single domain antibodies. In particular, the inventors isolated 3 different specific anti-EGFR clones binding to three distinct epitopes. Structure and sequences of said antibodies are depicted in FIG. 1A and Table 1. Interesting, the binding of all 3 sdAbs was found highly sensitive to ligand stimulation. Two sdabs, D10 and E10, can only bind the ligand-free EGFR conformation characterized by an intramolecular tether between domains II and IV, whereas sdAb G10 binds both ligand-free and ligand activated EGFR, with a eight-fold higher affinity for the extended conformation in the presence of ligand. Accordingly, these antibodies can be very useful for designing new diagnostic and therapeutic tools.

Table 1.

| Name | SEQ ID NO: | Sequence |
|---|---|---|
| D10 CDR1 | 1 | ISRTIFSLYA |
| D10 CDR2 | 2 | IYRSGDT |

-continued

| Name | SEQ ID NO: | Sequence |
|---|---|---|
| D10 CDR3 | 3 | NSPAQDWP |
| D10 | 4 | EVQLVESGG.GLVQAGGSLRLSCAVS ISRTIFSLYA<br>MEWYRQPPGKQRDLVAR IYRSGDT<br>NYADSVK.GRFTISRDNAKNTVYLQMNSLKPEDTGVYYC NSPAQDWP<br>WGQGTQVTVSS |
| G10 CDR1 | 5 | GRTFSNYA |
| G10 CDR2 | 6 | IIWSGSRT |
| G10 CDR3 | 7 | AASMGDYDVSLASPRS |
| G10 | 8 | EVQLVESGG.GLVQAGGSLRLSCAAS GRTFSNYA<br>MGWFRQAPGKEREFVAG IIWSGSRT<br>YYADPVK.GRFTISRDNAKNTVYLQMNSLNVEDTAVYYC<br>AASMGDYDVSLASPRS WGKGTQVTVSS |
| E10 CDR1 | 9 | GRTLSSYD |
| E10 CDR2 | 10 | INWGDLST |
| E10 CDR3 | 11 | AARLRYTVSDPIFSRPDRYNY |
| E10 | 12 | QVQLQESGG.GLAQAGGSLRLSCAAS GRTLSSYD<br>MGWFRQAPGKEREFVTA INWGDLST<br>YYADSVK.GRFTISRDNAKNTVYLQMNSLKPEDTAVYYC<br>AARLRYTVSDPIFSRPDRYNY WGQGTQVTVSS |

As used herein the term "single domain antibody" has its general meaning in the art and refers to the single heavy chain variable domain of antibodies of the type that can be found in Camelid mammals which are naturally devoid of light chains. Such single domain antibody are also called VHH or "Nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21(11):484-490; and WO 06/030220, WO 06/003388. The amino acid sequence and structure of a single domain antibody can be considered to be comprised of four framework regions or "FRs" which are referred to in the art and herein as "Framework region 1" or "FR1"; as "Framework region 2" or "FR2"; as "Framework region 3" or "FR3"; and as "Framework region 4" or "FR4" respectively; which framework regions are interrupted by three complementary determining regions or "CDRs", which are referred to in the art as "Complementarity Determining Region for "CDR1"; as "Complementarity Determining Region 2" or "CDR2" and as "Complementarity Determining Region 3" or "CDR3", respectively. Accordingly, the single domain antibody can be defined as an amino acid sequence with the general structure: FR1-CDR1-FR2-CDR2-FR3-CDR3-FR4 in which FR1 to FR4 refer to framework regions 1 to 4 respectively, and in which CDR1 to CDR3 refer to the complementarity determining regions 1 to 3. In the context of the invention, the amino acid residues of the single domain antibody are numbered according to the general numbering for VH domains given by the International ImMunoGeneTics information system aminoacid numbering (http://imgt.cines.fr/).

In particular, the present invention relates to an isolated single domain antibody ("D10 derivative") comprising a CDR1 having least 70% identity with sequence set forth as SEQ ID NO:1, a CDR2 having at least 70% identity with sequence set forth as SEQ ID NO:2 and a CDR3 having at least 70% identity with sequence set forth as SEQ ID NO:3.

In particular, the present invention relates to an isolated single domain antibody ("G10 derivative") comprising a CDR1 having least 70% identity with sequence set forth as SEQ ID NO:5, a CDR2 having at least 70% identity with sequence set forth as SEQ ID NO:6 and a CDR3 having at least 70% identity with sequence set forth as SEQ ID NO:7.

In particular, the present invention relates to an isolated single domain antibody ("E10 derivative") comprising a CDR1 having least 70% identity with sequence set forth as SEQ ID NO:9, a CDR2 having at least 70% identity with sequence set forth as SEQ ID NO:10 and a CDR3 having at least 70% identity with sequence set forth as SEQ ID NO:11.

According to the invention a first amino acid sequence having at least 70% identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99% identity with the second amino acid sequence. Amino acid sequence identity is typically determined using a suitable sequence alignment algorithm and default parameters, such as BLAST P (Karlin and Altschul, 1990).

In some embodiments the isolated single domain antibody (D10 derivative) according to the invention comprises a CDR1 having a sequence set forth as SEQ ID NO: 1, a CDR2 having a sequence set forth as SEQ ID NO:2 and a CDR3 having a sequence set forth as SEQ ID NO:3.

In some embodiments the isolated single domain antibody (G10 derivative) according to the invention comprises a CDR1 having a sequence set forth as SEQ ID NO:5, a CDR2 having a sequence set forth as SEQ ID NO:6 and a CDR3 having a sequence set forth as SEQ ID NO:7.

In some embodiments the isolated single domain antibody (E10 derivative) according to the invention comprises a CDR1 having a sequence set forth as SEQ ID NO:9, a CDR2 having a sequence set forth as SEQ ID NO:10 and a CDR3 having a sequence set forth as SEQ ID NO:11.

In some embodiments, the isolated single domain antibody according to the invention has the sequence set forth as SEQ ID NO:4 ("D10").

In some embodiments, the isolated single domain antibody according to the invention has the sequence set forth as SEQ ID NO:8 ("G10").

In some embodiments, the isolated single domain antibody according to the invention has the sequence set forth as SEQ ID NO:12. ("E10").

In some embodiments, the single domain antibody is a "humanized" single domain antibody. As used herein the term "humanized" refers to a single domain antibody of the invention wherein an amino acid sequence that corresponds to the amino acid sequence of a naturally occurring VHH domain has been "humanized", i.e. by replacing one or more amino acid residues in the amino acid sequence of said naturally occurring VHH sequence (and in particular in the framework sequences) by one or more of the amino acid residues that occur at the corresponding position(s) in a VH domain from a conventional chain antibody from a human being. Methods for humanizing single domain antibodies are well known in the art. Typically, the humanizing substitutions should be chosen such that the resulting humanized single domain antibodies still retain the favourable properties of single domain antibodies of the invention. The one skilled in the art is able to determine and select suitable humanizing substitutions or suitable combinations of humanizing substitutions. For example, the single domain antibodies of the invention may be suitably humanized at any framework residue depicted in FIG. 1A provided that the single domain antibodies remain soluble and do not significantly loss their affinity for EGFR.

A further aspect of the invention refers to a polypeptide comprising at least one single domain antibody of the invention.

Typically, the polypeptide of the invention comprises a single domain antibody of the invention, which is fused at its N terminal end, at its C terminal end, or both at its N terminal end and at its C terminal end to at least one further amino acid sequence, i.e. so as to provide a fusion protein. According to the invention the polypeptides that comprise a sole single domain antibody are referred to herein as "monovalent" polypeptides. Polypeptides that comprise or essentially consist of two or more single domain antibodies according to the invention are referred to herein as "multivalent" polypeptides.

In some embodiments, the polypeptide comprises at least one single domain antibody of the invention and at least one other binding unit (i.e. directed against another epitope, antigen, target, protein or polypeptide), which is typically also a single domain antibody. Such a polypeptide is referred to herein as "multispecific" polypeptide; in opposition to a polypeptide comprising the same single domain antibodies ("monospecific" polypeptide). Thus, in some embodiments, the polypeptide of the invention may also provide at least one further binding site directed against any desired protein, polypeptide, antigen, antigenic determinant or epitope. Said binding site is directed against to the same protein, polypeptide, antigen, antigenic determinant or epitope for which the single domain antibody of the invention is directed agains, or may be directed against a different protein, polypeptide, antigen, antigenic determinant or epitope) from the single domain antibody of the invention.

A "bispecific" polypeptide of the invention is a polypeptide that comprises at least one single domain antibody directed against a first antigen (i.e. EGFR) and at least one further binding site directed against a second antigen (i.e. different from EGFR), whereas a "trispecific" polypeptide of the invention is a polypeptide that comprises at least one single domain antibody directed against a first antigen (i.e. EGFR), at least one further binding site directed against a second antigen (i.e. different from EGFR) and at least one further binding site directed against a third antigen (i.e. different from both i.e. first and second antigen); etc.

In some embodiments, the further binding site is directed against an activating trigger molecule on an effector cell. Typically, said activating trigger molecule is selected from the group consisting of CD3, CD4, CD8, CD25, CD28, CD26, CTLA-4, ICOS, or CD11a. Other suitable antigens include but are not limited to those associated with immune cells including T cell-associated molecules, such as TCR/CD3 or CD2; NK cell-associated targets such as NKG2D, FcγRIIIa (CD16), CD38, CD44, CD56, or CD69; granulocyte-associated targets such as FcγRI (CD64), FcαRI (CD89), and CR3 (CD11b/CD18); monocyte/macrophage-associated targets (such as FcγRI (CD64), FcαRI (CD89), CD3 (CD11b/CD18), or mannose receptor; dendritic cell-associated targets such as FcγRI (CD64) or mannose receptor; and erythrocyte-associated targets such as CRI (CD35).

In some embodiments, the further binding site is directed against a serum protein so that the half-lie of the single domain antibody is increased. Typically, said serum protein is albumin.

Typically, the one or more further binding site may comprise one or more parts, fragments or domains of conventional chain antibodies (and in particular human antibodies) and/or of heavy chain antibodies. For example, a single domain antibody of the invention may be linked to a conventional (typically human) VH or VL optionally via a linker sequence.

In some embodiments, the polypeptides comprise a single domain antibody of the invention that is linked to an immunoglobulin domain. For example the polypeptides comprise a single domain antibody of the invention that is linked to an Fc portion (such as a human Fc). Said Fc portion may be useful for increasing the half-life and even the production of the single domain antibody of the invention. For example the Fc portion can bind to serum proteins and thus increases the half life on the single domain antibody. In some embodiments, the at least one single domain antibody may also be linked to one or more (typically human) CH1, and/or CH2 and/or CH3 domains, optionally via a linker sequence. For instance, a single domain antibody linked to a suitable CH1 domain could for example be used—together with suitable light chains—to generate antibody fragments/structures analogous to conventional Fab fragments or F(ab')2 fragments, but in which one or (in case of an F(ab')2 fragment) one or both of the conventional VH domains have been replaced by a single domain antibody of the invention. In some embodiments, one or more single domain antibodies of the invention may be linked (optionally via a suitable linker or hinge region) to one or more constant domains (for example, 2 or 3 constant domains that can be used as part of/to form an Fc portion), to an Fc portion and/or to one or more antibody parts, fragments or domains that confer one or more effector functions to the polypeptide of the invention and/or may confer the ability to bind to one or more Fc receptors. For example, for this purpose, and without being limited thereto, the one or more further amino acid sequences may comprise one or more CH2 and/or CH3 domains of an antibody, such as from a heavy chain antibody and more typically from a conventional human chain antibody; and/or may form and Fc region, for example from IgG (e.g. from IgG1, IgG2, IgG3 or IgG4), from IgE or from another human Ig such as IgA, IgD or IgM. For example, WO 94/04678 describes heavy chain antibodies comprising a Camelid VHH domain or a humanized derivative thereof (i.e. a single domain antibody), in which the Camelidae CH2 and/or CH3 domain have been replaced by human CH2 and CH3 domains, so as to provide an immunoglobulin that consists of 2 heavy chains each comprising a single domain antibody and human CH2 and CH3 domains (but no CHI domain), which immunoglobulin has the effector function provided by the CH2 and CH3 domains and which immunoglobulin can function without the presence of any light chains.

In some embodiment, the polypeptide is as described in WO2006064136. In particular the polypeptide may consist of i) a first fusion protein wherein the CL constant domain of an antibody is fused by its N-terminal end to the C-terminal end to a single domain antibody according to the invention (i.e. a single antibody directed against EGFR) and ii) a second fusion protein wherein the CH1 constant domain of an antibody is fused by its N-terminal end to the C-terminal end of a single domain antibody directed against an antigen different from EGFR. In another particular embodiment, the polypeptide consists of a first fusion protein wherein the CH1 constant domain of an antibody is fused by its N-terminal end to the C-terminal end of a single domain antibody directed against a an activating trigger molecule on an effector cell (e.g. CD16) and a second fusion protein wherein the CL constant domain of an antibody is fused by its N-terminal end to the C-terminal end to a single domain antibody of the invention (i.e. EGFR).

In some embodiments, the polypeptide is a biparatopic polypeptide. As used herein, the term "biparatopic" polypeptide means a polypeptide comprising a single domain antibody and a second single domain antibody as herein defined, wherein these two single domain antibodies are capable of binding to two different epitopes of one antigen (e.g. EGFR), which epitopes are not normally bound at the same time by one monospecific immunoglobulin, such as e.g. a conventional antibody or one single domain antibody. The biparatopic polypeptides according to the invention are composed of single domain antibodies which have different epitope specificities, and do not contain mutually complementary variable domain pairs which bind to the same epitope. They do therefore not compete with each other for binding to EGFR.

In some embodiments, the biparatopic polypeptide of the present invention comprises a D10 derivative as defined above and a E10 derivative as defined above. In some embodiments, the biparatopic polypeptide of the present invention comprises i) a first single domain antibody comprising a CDR1 having least 70% identity with sequence set forth as SEQ ID NO:1, a CDR2 having at least 70% identity with sequence set forth as SEQ ID NO:2 and a CDR3 having at least 70% identity with sequence set forth as SEQ ID NO:3 and ii) a second single domain antibody ("E10 derivative") comprising a CDR1 having least 70% identity with sequence set forth as SEQ ID NO:9, a CDR2 having at least 70% of identity with sequence set forth as SEQ ID NO:10 and a CDR3 having at least 70% identity with sequence set forth as SEQ ID NO:11. In some embodiments, the biparatopic antibody of the present invention comprises i) a first single domain antibody comprising a CDR1 having a sequence set forth as SEQ ID NO: 1, a CDR2 having a sequence set forth as SEQ ID NO:2 and a CDR3 having a sequence set forth as SEQ ID NO:3 and ii) a second single domain antibody comprising a CDR1 having a sequence set forth as SEQ ID NO:9, a CDR2 having a sequence set forth as SEQ ID NO:10 and a CDR3 having a sequence set forth as SEQ ID NO:11. In some embodiments, the biparatopic polypeptide of the present invention comprises i) a first single domain antibody having the sequence set forth as SEQ ID NO:4 and ii) a second single domain antibody having the sequence set forth as SEQ ID NO:12.

In some embodiments, the two single domain antibodies of the biparatopic polypeptide of the present invention can be linked to each other directly (i.e. without use of a linker) or via a linker. The linker is typically a linker peptide and will, according to the invention, be selected so as to allow binding of the two single domain antibodies to each of their at least two different epitopes of EGFR. Suitable linkers inter alia depend on the epitopes and, specifically, the distance between the epitopes on EGFR to which the single domain antibodies bind, and will be clear to the skilled person based on the disclosure herein, optionally after some limited degree of routine experimentation. Also, when the two single domain antibodies that bind to EGFR may also be linked to each other via a third single domain antibody (in which the two single domain antibodies may be linked directly to the third domain antibody or via suitable linkers). Such a third single domain antibody may for example be a single domain antibody that provides for an increased half-life. For example, the latter single domain antibody may be a single domain antibody that is capable of binding to a (human) serum protein such as (human) serum albumin or (human) transferrin, as further described herein. In some embodiments, two or more single domain antibodies that bind to EGFR are linked in series (either directly or via a suitable linker) and the third (single) single domain antibody (which may provide for increased half-life, as decribed above) is connected directly or via a linker to one of these two or more aforementioned single domain antibodies. Suitable linkers are described herein in connection with specific polypeptides of the invention and may—for example and without limitation—comprise an amino acid sequence, which amino acid sequence preferably has a length of 9 or more amino acids, more preferably at least 17 amino acids, such as about 20 to 40 amino acids. However, the upper limit is not critical but is chosen for reasons of convenience regarding e.g. biopharmaceutical production of such polypeptides. The linker sequence may be a naturally occurring sequence or a non-naturally occurring sequence. If used for therapeutical purposes, the linker is preferably non-immunogenic in the subject to which the anti-EGFR polypeptide of the invention is administered. One useful group of linker sequences are linkers derived from the hinge region of heavy chain antibodies as described in WO 96/34103 and WO 94/04678. Other examples are poly-alanine linker sequences such as Ala-Ala-Ala. Further preferred examples of linker sequences are Gly/Ser linkers of different length including (gly4ser)3, (gly4ser)4, (gly4ser), (gly3ser), gly3, and (gly3ser2)3.

In some embodiments, the biparatopic polypeptide has a sequence selected from the group consisting of SEQ ID NO:12, SEQ ID NO:13 and SEQ ID NO:14.

In some embodiments, it is contemplated that the polypeptides of the invention used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications. Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 45 kDa). In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes (see e.g., technologies of established by VectraMed, Plainsboro, N.J.). Such linkers may be used in modifying the polypeptide of the invention described herein for therapeutic delivery.

According to the invention, the single domain antibodies and polypeptides of the invention may be produced by conventional automated peptide synthesis methods or by recombinant expression. General principles for designing and making proteins are well known to those of skill in the art.

The single domain antibodies and polypeptides of the invention may be synthesized in solution or on a solid support in accordance with conventional techniques. Various automatic synthesizers are commercially available and can be used in accordance with known protocols as described in Stewart and Young; Tam et al., 1983; Merrifield, 1986 and Barany and Merrifield, Gross and Meienhofer, 1979. The single domain antibodies and polypeptides of the invention may also be synthesized by solid-phase technology employing an exemplary peptide synthesizer such as a Model 433A from Applied Biosystems Inc. The purity of any given protein; generated through automated peptide synthesis or through recombinant methods may be determined using reverse phase HPLC analysis. Chemical authenticity of each peptide may be established by any method well known to those of skill in the art.

As an alternative to automated peptide synthesis, recombinant DNA technology may be employed wherein a nucleotide sequence which encodes a protein of choice is inserted into an expression vector, transformed or transfected into an appropriate host cell and cultivated under conditions suitable for expression as described herein below. Recombinant methods are especially preferred for producing longer polypeptides.

A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors (Giga-Hama et al., 1999); insect cell systems infected with virus expression vectors (e.g., baculovirus, see Ghosh et al., 2002);

plant cell systems transfected with virus expression vectors (e.g., cauliflower mosaic virus, CaMV; tobacco mosaic virus, TMV) or transformed with bacterial expression vectors (e.g., Ti or pBR322 plasmid; see e.g., Babe et al., 2000); or animal cell systems. Those of skill in the art are aware of various techniques for optimizing mammalian expression of proteins, see e.g., Kaufman, 2000; Colosimo et al., 2000. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the peptide substrates or fusion polypeptides in bacteria, yeast and other invertebrates are known to those of skill in the art and a briefly described herein below. Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

In the recombinant production of the single domain antibodies and polypeptides of the invention, it would be necessary to employ vectors comprising polynucleotide molecules for encoding the single domain antibodies and polypeptides of the invention. Methods of preparing such vectors as well as producing host cells transformed with such vectors are well known to those skilled in the art. The polynucleotide molecules used in such an endeavor may be joined to a vector, which generally includes a selectable marker and an origin of replication, for propagation in a host. These elements of the expression constructs are well known to those of skill in the art. Generally, the expression vectors include DNA encoding the given protein being operably linked to suitable transcriptional or translational regulatory sequences, such as those derived from a mammalian, microbial, viral, or insect genes. Examples of regulatory sequences include transcriptional promoters, operators, or enhancers, mRNA ribosomal binding sites, and appropriate sequences which control transcription and translation.

The terms "expression vector," "expression construct" or "expression cassette" are used interchangeably throughout this specification and are meant to include any type of genetic construct containing a nucleic acid coding for a gene product in which part or all of the nucleic acid encoding sequence is capable of being transcribed.

The choice of a suitable expression vector for expression of the peptides or polypeptides of the invention will of course depend upon the specific host cell to be used, and is within the skill of the ordinary artisan.

Expression requires that appropriate signals be provided in the vectors, such as enhancers/promoters from both viral and mammalian sources that may be used to drive expression of the nucleic acids of interest in host cells. Usually, the nucleic acid being expressed is under transcriptional control of a promoter. A "promoter" refers to a DNA sequence recognized by the synthetic machinery of the cell, or introduced synthetic machinery, required to initiate the specific transcription of a gene. Nucleotide sequences are operably linked when the regulatory sequence functionally relates to the DNA encoding the protein of interest (e.g., a single domain antibody). Thus, a promoter nucleotide sequence is operably linked to a given DNA sequence if the promoter nucleotide sequence directs the transcription of the sequence.

In another aspect, the present invention provides antibody-drug conjugate. An "anti-EGFR antibody-drug conjugate" as used herein refers to an anti-EGFR single domain antibody or polypeptide of the present invention conjugated to a therapeutic agent. Such anti-EGFR antibody drug conjugates produce clinically beneficial effects on EGFR-expressing cells when administered to a subject, such as, for example, a subject with a EGFR-expressing cancer, typically when administered alone but also in combination with other therapeutic agents. In some embodiments, an anti-EGFR single domain antibody or polypeptide of the present invention is conjugated to a cytotoxic agent, such that the resulting drug conjugate exerts a cytotoxic or cytostatic effect on a EGFR-expressing cell {e.g., a EGFR-expressing cancer cell) when taken up or internalized by the cell. Particularly suitable moieties for conjugation to antibodies are chemotherapeutic agents, prodrug converting enzymes, radioactive isotopes or compounds, or toxins. For example, an anti-EGFR single domain antibody or polypeptide of the present invention can be conjugated to a cytotoxic agent such as a chemotherapeutic agent or a toxin (e.g., a cytostatic or cytocidal agent such as, for example, abrin, ricin A, pseudomonas exotoxin, or diphtheria toxin). Useful classes of cytotoxic agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and-carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like. Individual cytotoxic agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065 (Li et al., Cancer Res. 42:999-1004, 1982), chlorambucil, cisp latin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, etopside phosphate (VP-16), 5-fluoro uracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide (VM-26), 6-thioguanine, thioTEPA, topotecan, vinblastine, vincristine, and vinorelbine. Particularly suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, vinca alkaloids, CC-1065, SN-38 (7-ethyl-lO-hydroxy-camptothein), topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, disco dermolide, eleutherobin, and mitoxantrone. In some embodiments, a cytotoxic agent is a conventional chemotherapeutic such as, for example, doxorubicin, paclitaxel, melphalan, vinca alkaloids, methotrexate, mitomycin C or etoposide. In addition, potent agents such as CC-1065 analogues, calicheamicin, maytansine, analogues of dolastatin 10, rhizoxin, and palytoxin can be linked to an anti-EGFR-expressing antibody. In specific variations, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP (dimethylvaline-valine-dolaisoleuine-dolaproine-phenylalanine-p-phenylenediamine), MMAF (dovaline-valine-dolaisoleunine-dolaproine-phenylalanine), and MAE (monomethyl auristatin E). The synthesis and structure of auristatin E and its derivatives are described in U.S. Patent Application Publication No. 20030083263; International Patent Publication Nos. WO 2002/088172 and WO 2004/010957; and U.S. Pat. Nos. 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414. In other variations, the cytotoxic agent is a DNA minor groove binding agent. (See, e.g., U.S. Pat. No. 6,130,237.) For example, in some embodiments, the minor groove binding agent is a CBI compound. In some embodiments, the minor groove binding agent is an enediyne (e.g., calicheamicin). In some embodiments, an antibody-drug conjugate comprises an anti-tubulin agent. Examples of anti-tubulin agents include, for example, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin. In some embodiments, the cytotoxic agent is a maytansinoid, another group of antitubulin agents. For example, in specific embodiments, the maytansinoid is maytansine or DM-1 (ImmunoGen, Inc.; see also Chari et ah, Cancer Res. 52: 127-131, 1992). In some embodiments, the cytotoxic agent is an antimetabolite. The antimetabolite can be, for example, a purine antagonist (e.g., azothioprine or mycophenolate mofetil), a dihydro folate reductase inhibitor (e.g., methotrexate), acyclovir, gangcyclovir, zidovudine, vidarabine, ribavarin, azido thymidine, cytidine arabinoside, amantadine, dideoxyuridine, iododeoxyuridine, poscarnet, or trifluridine.

In some embodiments, an anti-EGFR single domain antibody or polypeptide of the present invention is conjugated to a pro-drug converting enzyme. The pro-drug converting enzyme can be recombinantly fused to the antibody or chemically conjugated thereto using known methods. Exemplary pro-drug converting enzymes are carboxypeptidase G2, β-glucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. {See, e.g., Arnon et al., "Monoclonal Antibodies For Immunotargeting Of Drugs In Cancer Therapy," in Monoclonal Antibodies And Cancer Therapy (Reisfeld et al. eds., Alan R. Liss, Inc., 1985); Hellstrom et al, "Antibodies For Drug Delivery," in Controlled Drug Delivery (Robinson et al. eds., Marcel Deiker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radiolabeled Antibody In Cancer Therapy," in Monoclonal Antibodies For Cancer Detection And Therapy (Baldwin et al. eds., Academic Press, 1985); and Thorpe et al., 1982, Immunol. Rev. 62:119-58. See also, e.g., PCT publication WO 89/12624.)

Diagnostic uses:

A further aspect of the present invention relates to an isolated single domain antibody comprising a CDR1 having least 70% identity with sequence set forth as SEQ ID NO:1, a CDR2 having at least 70% identity with sequence set forth as SEQ ID NO:2 and a CDR3 having at least 70% identity with sequence set forth as SEQ ID NO:3 for use as an inhibitor of EGFR inhibitor. In some embodiments the isolated single domain antibody according to the invention comprises a CDR1 having a sequence set forth as SEQ ID NO: 1, a CDR2 having a sequence set forth as SEQ ID NO:2 and a CDR3 having a sequence set forth as SEQ ID NO:3 is used as an inhibitor of EGFR. In some embodiments, the isolated single domain antibody according to the invention has the sequence set forth as SEQ ID NO:4 is used as an an inhibitor of EGFR.

A further aspect of the present invention relates to an isolated single domain antibody comprising a CDR1 having least 70% identity with sequence set forth as SEQ ID NO:9, a CDR2 having at least 70% identity with sequence set forth as SEQ ID NO:10 and a CDR3 having at least 70% identity with sequence set forth as SEQ ID NO:11 for use as an inhibitor of EGFR. In some embodiments the isolated single domain antibody according to the invention comprises a CDR1 having a sequence set forth as SEQ ID NO:9, a CDR2 having a sequence set forth as SEQ ID NO:10 and a CDR3 having a sequence set forth as SEQ ID NO:11 is used as an inhibitor of EGFR. In some embodiments, the isolated single domain antibody according to the invention has the sequence set forth as SEQ ID NO:12 is used as an inhibitor of EGFR.

The single domain antibodies and polypeptides of the invention are particularly suitable for the treatment of cancers. EGFR expression has been observed in a variety of human tumors, both in vitro and in vivo, and the levels of EGFR expression vary widely with tumor type. EGFR is expressed at varying levels on the cell surface in a significant percentage of human tumors, such as colorectal, head and neck (squamous cell), pancreatic, lung, breast, and renal cell carcinomas, as well as glioblastoma. In certain tumor types, EGFR expression is very common (e.g., 35% to 70% of ovarian cancers and approximately 25% to 77% of colorectal cancers). High levels of EGFR expression can occur in correlation with production of receptor ligands (i.e., EGF and TGF-α). EGFR expression has also been correlated with increased resistance to certain chemotherapeutic agents and radiotherapy. EGFR expression may also serve as a prognostic factor in certain types of tumors, as it has be associated with reduced survival, poor prognosis, and/or increased risk of metastasis. Moreover, increased EGFR expression exists in multiple tumor types. Accordingly a further aspect of the present invention relates to a method of treating tumor growth in a patient in need thereof by administering to the patient a therapeutically effective amount of a single domain antibody or polypeptide of the invention. Suitable cancers to be treated according to the present invention express EGFR. Treatment of such tumors according to the invention includes partial or complete inhibition of tumor growth. Notably, in some embodiments, inhibition further includes tumor regression.

Tumors to be treated include primary tumors and metastatic tumors, as well as refractory tumors. Refractory tumors include tumors that fail to respond or are resistant to treatment with chemotherapeutic agents alone, antibodies alone, radiation alone or combinations thereof. Refractory tumors also encompass tumors that appear to be inhibited by treatment with such agents, but recur up to five years, sometimes up to ten years or longer after treatment is discontinued. Examples of cancers that may be treated by methods and compositions of the invention include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangio sarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The present invention also provides a method of treating a non-cancer hyperproliferative disease in a patient comprising administering to the patient an effective amount of the single domain antibody or polypeptide of the present invention. As disclosed herein, "hyperproliferative disease" is defined as a condition caused by excessive growth of non-cancer cells that express a member of the EGFR family of receptors. The excess cells generated by a hyperproliferative disease express EGFR at normal levels or they may overexpress EGFR. The types of hyperproliferative diseases that can be treated in accordance with the invention are any hyperproliferative diseases that are stimulated by a ligand of EGFR or mutants of such ligands. Examples of hyperproliferative disease include psoriasis, actinic keratoses, and seborrheic keratoses, warts, keloid scars, and eczema. Also included are hyperproliferative diseases caused by virus infections, such as papilloma virus infection. For example, psoriasis comes in many different variations and degrees of severity. Different types of psoriasis display characteristics such as pus-like blisters (pustular psoriasis), severe sloughing of the skin (erythrodermic psoriasis), drop-like dots (guttae psoriasis) and smooth inflamed lesions (inverse psoriasis). The treatment of all types of psoriasis (e. g., psoriasis vulgaris, psoriasis pustulosa, psoriasis erythrodermica, psoriasis arthropathica, parapsoriasis, palnoplantar pustulosis) is contemplated by the invention.

In some embodiments, the single domain antibody or the polypeptide of the present invention is used in combination with a HER inhibitor.

As used herein the "HER" has its general meaning in the art and refers to a receptor protein tyrosine kinase which belongs to the HER receptor family and includes EGFR, HER2, HER3 and HER4 receptors. As used herein the terms "ErbB1," "HER1", "epidermal growth factor receptor" and "EGFR" are used interchangeably herein and refer to EGFR as disclosed, for example, in Carpenter et al. Ann. Rev. Biochem. 56:881-914 (1987), As used herein, the terms "ErbB2" and "HER2" are used interchangeably herein and refer to human HER2 protein described, for example, in Semba et al., PNAS (USA) 82:6497-6501 (1985) and Yamamoto et al. Nature 319:230-234 (1986) (Genebank accession number X03363). As used herein, the term "ErbB3" and "HER3" refer to the receptor polypeptide as disclosed, for example, in U.S. Pat. Nos. 5,183,884 and 5,480,968 as well as Kraus et al. PNAS (USA) 86:9193-9197 (1989). As used herein, the terms "ErbB4" and "HER4" refer to the receptor polypeptide as disclosed, for example, in EP Pat Appln No 599,274; Plowman et al., Proc. Natl. Acad. Sci. USA, 90:1746-1750 (1993); and Plowman et al., Nature, 366:473-475 (1993). By "HER ligand" is meant a polypeptide which binds to and/or activates a HER receptor.

As used herein the term "HER inhibitor" refers to an agent which interferes with HER activation or function. Examples of HER inhibitors include HER antibodies (e.g. EGFR, HER2, HER3, or HER4 antibodies); small organic molecule HER antagonists; HER tyrosine kinase inhibitors; HER2 and EGFR dual tyrosine kinase inhibitors such as lapatinib/GW572016; antisense molecules (see, for example, WO2004/87207); and/or agents that bind to, or interfere with function of, downstream signaling molecules, such as MAPK or Akt. Typically, the HER inhibitor is an antibody or small organic molecule which binds to a HER receptor. In some embodiments, the HER inhibitor is a "HER dimerization inhibitor" which is an agent which inhibits formation of a HER dimer or HER heterodimer.

In some embodiments, the HER inhibitor is an "anti-HER antibody" which is an antibody that binds to a HER receptor. In some embodiments, the anti-HER monoclonal antibody of the present invention is used to induce antibody dependent cellular cytotoxicity (ADCC) or complement dependent cytotoxicity (CDC) against HER-expressing cells. In another particular embodiment, the anti-HER antibody may be suitable for disturbing the expression of HER at the cell surface (e.g. by provoking internalization of HER) so that cell migration, cell proliferation and tumour growth of tumor cells will be limited or inhibited.

In some embodiments, the anti-HER antibody is an anti-HER monoclonal antibody-drug conjugate. An "anti-HER monoclonal antibody-drug conjugate" as used herein refers to an anti-HER monoclonal antibody according to the invention conjugated to a therapeutic agent. Such anti-HER monoclonal antibody-drug conjugates produce clinically beneficial effects on HER-expressing tumor cells when administered to a subject. In typical embodiments, an anti-HER monoclonal antibody is conjugated to a cytotoxic agent, such that the resulting antibody-drug conjugate exerts a cytotoxic or cytostatic effect on a HER-expressing tumor cell when taken up or internalized by the cell. Any cytotoxic agent well known by the skilled person may used. In some embodiments, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP (dimethylvaline-valine-dolaisoleuine-dolaproine-phenylalanine-p-phenylenediamine), MMAF (dovaline-valine-dolaisoleuine-dolaproine-phenylalanine), and MAE (monomethyl auristatin E). The synthesis and structure of auristatin E and its derivatives are described in U.S. Patent Application Publication No. 20030083263; International Patent Publication Nos. WO 2002/088172 and WO 2004/010957; and U.S. Pat. Nos. 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

Patent publications related to HER antibodies include: U.S. Pat. Nos. 5,677,171, 5,720,937, 5,720,954, 5,725,856, 5,770,195, 5,772,997, 6,165,464, 6,387,371, 6,399,063, US2002/0192211A1, U.S. Pat. Nos. 6,015,567, 6,333,169, 4,968,603, 5,821,337, 6,054,297, 6,407,213, 6,719,971, 6,800,738, US2004/0236078A1, U.S. Pat. Nos. 5,648,237, 6,267,958, 6,685,940, 6,821,515, WO98/17797, U.S. Pat. Nos. 6,127,526, 6,333,398, 6,797,814, U.S. Pat. No. 6,339,142, 6,417,335, 6,489,447, WO99/31140, US2003/0147884A1, US2003/0170234A1, US2005/0002928A1, U.S. Pat. No. 6,573,043, US2003/0152987A1, WO99/48527, US2002/0141993A1, WO01/00245, US2003/0086924, US2004/0013667A1, WO00/69460, WO01/00238, WO01/15730, U.S. Pat. No. 6,627,196B1, U.S. Pat. No. 6,632,979B1, WO01/00244, US2002/0090662A1, WO01/89566, US2002/0064785, US2003/0134344, WO 04/24866, US2004/0082047, US2003/0175845A1, WO03/087131, US2003/0228663, WO2004/008099A2, US2004/0106161, WO2004/048525, US2004/0258685A1, U.S. Pat. Nos. 5,985,553, 5,747,261, 4,935,341, 5,401,638, 5,604,107, WO 87/07646, WO 89/10412, WO 91/05264, EP 412,116 B1, EP 494,135 B1, U.S. Pat. No. 5,824,311, EP 444,181 B1, EP 1,006,194 A2, US 2002/0155527A1, WO 91/02062, U.S. Pat. Nos. 5,571,894, 5,939,531, EP 502,812 B1, WO 93/03741, EP 554,441 B1, EP 656,367 A1, U.S. Pat. Nos. 5,288,477, 5,514,554, 5,587,458, WO 93/12220, WO 93/16185, U.S. Pat. No. 5,877,305, WO 93/21319, WO 93/21232, U.S. Pat. No. 5,856,089, WO 94/22478, U.S. Pat. Nos. 5,910,486, 6,028,059, WO 96/07321, U.S. Pat. Nos. 5,804,396, 5,846,749, EP 711,565, WO 96/16673, U.S. Pat. Nos. 5,783,404, 5,977,322, 6,512,097, WO 97/00271, U.S. Pat. Nos. 6,270,765, 6,395,272, 5,837,243, WO 96/40789, U.S. Pat. Nos. 5,783,186, 6,458,356, WO 97/20858, WO 97/38731, U.S. Pat. Nos. 6,214,388, 5,925,519, WO 98/02463, U.S. Pat. No. 5,922,845, WO 98/18489, WO 98/33914, U.S. Pat. No. 5,994,071, WO 98/45479, U.S. Pat. No. 6,358,682 B1, US 2003/0059790, WO 99/55367, WO 01/20033, US 2002/0076695 A1, WO 00/78347, WO 01/09187, WO 01/21192, WO 01/32155, WO 01/53354, WO 01/56604, WO 01/76630, WO02/05791, WO 02/11677, U.S. Pat. No. 6,582,919, US2002/0192652A1, US 2003/0211530A1, WO 02/44413, US 2002/0142328, U.S. Pat. No. 6,602,670 B2, WO 02/45653, WO 02/055106, US 2003/0152572, US 2003/0165840, WO 02/087619, WO 03/006509, WO03/012072, WO 03/028638, US 2003/0068318, WO 03/041736, EP 1,357,132, US 2003/0202973, US 2004/0138160, U.S. Pat. Nos. 5,705,157, 6,123,939, EP 616,812 B1, US 2003/0103973, US 2003/0108545, U.S. Pat. No. 6,403,630 B1, WO 00/61145, WO 00/61185, U.S. Pat. No. 6,333,348 B1, WO 01/05425, WO 01/64246, US 2003/0022918, US 2002/0051785 A1, U.S. Pat. No. 6,767,541, WO 01/76586, US 2003/0144252, WO 01/87336, US 2002/0031515 A1, WO 01/87334, WO 02/05791, WO 02/09754, US 2003/0157097, US 2002/0076408, WO 02/055106, WO 02/070008, WO 02/089842, WO 03/86467, WO2013164689, WO2012059857.

In some embodiments, the HER inhibitor is a small organic molecule. As used herein, the term "small organic molecule" refers to a molecule of size comparable to those organic molecules generally sued in pharmaceuticals. The term excludes biological macromolecules (e.g.; proteins, nucleic acids, etc.); preferred small organic molecules range in size up to 2000 da, and most preferably up to about 1000 Da.

In some embodiments, the HER inhibitor is tyrosine kinase inhibitor. A "tyrosine kinase inhibitor" is a molecule which inhibits tyrosine kinase activity of the HER receptor. Examples of such inhibitors include the small organic molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; GW572016 (available from Glaxo) an oral HER2 and EGFR tyrosine kinase inhibitor; PKI-166 (available from Novartis); pan-HER inhibitors such as canertinib (CI-1033; Pharmacia); non selective HER inhibitors such as Imatinib mesylate (Gleevec™); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino) phthalimide); tyrphostines containing nitrothiophene moieties; PD-0183805 (Warner-Lamber); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); PKI 166 (Novartis); GW2016 (Glaxo SmithKline); CI-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804,396; WO99/09016 (American Cyanimid); WO98/43960 (American Cyanamid); WO97/38983 (Warner Lambert); WO99/06378 (Warner Lambert); WO99/06396 (Warner Lambert); WO96/30347 (Pfizer, Inc); WO96/33978 (Zeneca); WO96/3397 (Zeneca); and WO96/33980 (Zeneca).

In some embodiments, the HER inhibitor is an EGFR inhibitor. GFR inhibitors are well known in the art (Inhibitors of erbB-1 kinase; Expert Opinion on Therapeutic Patents December 2002, Vol. 12, No. 12, Pages 1903-1907, Susan E Kane. Cancer therapies targeted to the epidermal growth factor receptor and its family members. Expert Opinion on Therapeutic Patents February 2006, Vol. 16, No. 2, Pages 147-164. Peter Traxler Tyrosine kinase inhibitors in cancer treatment (Part II). Expert Opinion on Therapeutic Patents December 1998, Vol. 8, No. 12, Pages 1599-1625). Examples of such agents include antibodies and small organic molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO98/50433, Abgenix); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding; and mAb 806 or humanized mAb 806 (Johns et al., J. Biol. Chem. 279(29):30375-30384 (2004)). The anti-EGFR antibody may be conjugated with a cytotoxic agent, thus generating an immunoconjugate (see, e.g., EP659,439A2, Merck Patent GmbH). Examples of small organic molecules that bind to EGFR include ZD1839 or Gefitinib (IRESSA™; Astra Zeneca); CP-358774 or erlotinib (TARCEVA™; Genentech/OSI); and AG1478, AG1571 (SU 5271; Sugen); EMD-7200. In some embodiments, the HER inhibitor is a small organic molecule pan-HER inhibitor such as dacomitinib (PF-00299804).

In some embodiments, the HER inhibitor is selected from the group consisting of cetuximab, panitumumab, zalutumumab, nimotuzumab, erlotinib, gefitinib, lapatinib, neratinib, canertinib, vandetanib, afatinib, TAK-285 (dual HER2 and EGFR inhibitor), ARRY334543 (dual HER2 and EGFR inhibitor), Dacomitinib (pan-ErbB inhibitor), OSI-420 (Desmethyl Erlotinib) (EGFR inhibitor), AZD8931 (EGFR, HER2 and HER3 inhibitor), AEE788 (NVP-AEE788) (EGFR, HER2 and VEGFR 1/2 inhibitor), Pelitinib (EKB-569) (pan-ErbB inhibitor), CUDC-101 (EGFR, HER2 and HDAC inhibitor), XL647 (dual HER2 and EGFR inhibitor), BMS-599626 (AC480) (dual HER2 and EGFR inhibitor), PKC412 (EGFR, PKC, cyclic AMP-dependent protein kinase and S6 kinase inhibitor), BIBX1382 (EGFR inhibitor) and AP261 13 (ALK and EGFR inhibitor). The inhibitors cetuximab, panitumumab, zalutumumab, nimotuzumab are monoclonal antibodies. erlotinib, gefitinib, lapatinib, neratinib, canertinib, vandetanib and afatinib are tyrosine kinase inhibitors.

According to the invention single domain antibody of the invention or the polypeptide of the invention is administered to the patient with a therapeutically effective amount. By a "therapeutically effective amount" is meant a sufficient amount of the single domain antibody of the invention or the polypeptide of the invention to treat the disease (e.g. cancer) at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular patient will depend upon a variety of factors including the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, typically from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The single domain antibodies and polypeptides of the invention or the polypeptide of the present may be combined with pharmaceutically acceptable excipients, and optionally sustained-release matrices, such as biodegradable polymers, to form phamaceutical compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The polypeptide (or nucleic acid encoding thereof) can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

In further aspect of the present invention, there is provided a method of diagnosing a disease, disorder or condition mediated by EGFR (e.g. cancer) comprising the steps of i) a) obtaining a sample from the subject, ii) contacting, in vitro, the sample with a single domain antibody or polypeptide of the present invention, iii) detecting the binding of said single domain antibody or polypeptide to said sample, and iv) comparing the binding detected in step (iii) with a standard, wherein a difference in binding relative to said sample is diagnostic of a disease, disorder or condition characterized by EGFR.

As used herein the term "sample" encompasses a variety of sample types obtained from a subject and can be used in a diagnostic or monitoring assay. Biological samples include but are not limited to blood and other liquid samples of biological origin, solid tissue samples such as a biopsy specimen or tissue cultures or cells derived therefrom, and the progeny thereof. In some embodiments, the sample is a tumor tissue sample when the subject suffers from a cancer. The term "tumor sample" means any tissue sample derived from the tumor of the subject. The tissue sample is obtained for the purpose of the in vitro evaluation and typically results from biopsy performed in a tumor of the subject. The sample can be fresh, frozen, or embedded (e.g., FFPE biopsy).

In some embodiments, the single domain antibody or polypeptide of the present invention can be conjugated with a detectable label to form an anti-EGFR immuno conjugate. Suitable detectable labels include, for example, a radioisotope, a fluorescent label, a chemiluminescent label, an enzyme label, a bio luminescent label or colloidal gold. Methods of making and detecting such detectably-labeled immunoconjugates are well-known to those of ordinary skill in the art, and are described in more detail below. For instance, the detectable label can be a radioisotope that is detected by autoradiography. Isotopes that are particularly useful for the purpose of the present invention are 3 H, 125 I, 131 I, 35S and 14C. Anti-EGFR immunoconjugates can also be labeled with a fluorescent compound. The presence of a fluorescently-labeled single domain antibody or polypeptide of the present invention is determined by exposing the immuno conjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine and Alexa Fluor dyes. Alternatively, anti-EGFR immunoconjugates can be detectably labeled by coupling an single domain antibody or polypeptide of the present invention to a chemiluminescent compound. The presence of the chemiluminescent-tagged immuno conjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester. Similarly, a bio luminescent compound can be used to label anti-EGFR immunoconjugates of the present invention. Bio luminescence is a type of chemiluminescence found in biological systems in which a catalytic protein increases the efficiency of the chemiluminescent reaction. The presence of a bio luminescent protein is determined by detecting the presence of luminescence. Bio luminescent compounds that are useful for labeling include luciferin, luciferase and aequorin. Alternatively, anti-EGFR immunoconjugates can be detectably labeled by linking an anti-EGFR single domain antibody or polypeptide of the present invention to an enzyme. When the anti-EGFR-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase. Those of skill in the art will know of other suitable labels which can be employed in accordance with the present invention. The binding of marker moieties to anti-EGFR single domain antibodies or polypeptides of the present invention can be accomplished using standard techniques known to the art. Typical methodology in this regard is described by Kennedy et al., Clin. Chim. Acta 70: 1, 1976; Schurs et al., Clin. Chim. Acta 81: 1, 1977; Shih et al., Int'U. Cancer 46: 1101, 1990; Stein et al, Cancer Res. 50: 1330, 1990; and Coligan, supra. Moreover, the convenience and versatility of immunochemical detection can be enhanced by using anti-EGFR single domain antibodies or polypeptides of the present invention that have been conjugated with avidin, streptavidin, and biotin. {See, e.g., Wilchek et al. (eds.), "Avidin-Biotin Technology," Methods In Enzymology (Vol. 184) (Academic Press 1990); Bayer et al., "Immunochemical Applications of Avidin-Biotin Technology," in Methods In Molecular Biology (Vol. 10) 149-162 (Manson, ed., The Humana Press, Inc. 1992).)

Methods for performing immunoassays are well-established. {See, e.g., Cook and Self, "Monoclonal Antibodies in Diagnostic Immunoassays," in Monoclonal Antibodies: Production, Engineering, and Clinical Application 180-208 (Ritter and Ladyman, eds., Cambridge University Press 1995); Perry, "The Role of Monoclonal Antibodies in the Advancement of Immunoassay Technology," in Monoclonal Antibodies: Principles and Applications 107-120 (Birch and Lennox, eds., Wiley-Liss, Inc. 1995); Diamandis, Immunoassay (Academic Press, Inc. 1996).)

In particular, the single domain antibodies or polypeptides of the present invention which are capable to recognize the active form of EGFR may be used for determining whether the subject is eligible for a treatment with a EGFR inhibitor by performing a diagnostic method as above described. In some embodiments the EGFR inhibitor is a single domain antibody or polypeptide of the present invention.

The invention will be further illustrated by the following figures and examples. However, these examples and figures should not be interpreted in any way as limiting the scope of the present invention.

FIGURES

FIG. 1A shows the structure and sequences of the anti-EGFR sdAb D10, E10, G10.

Figure 1C:
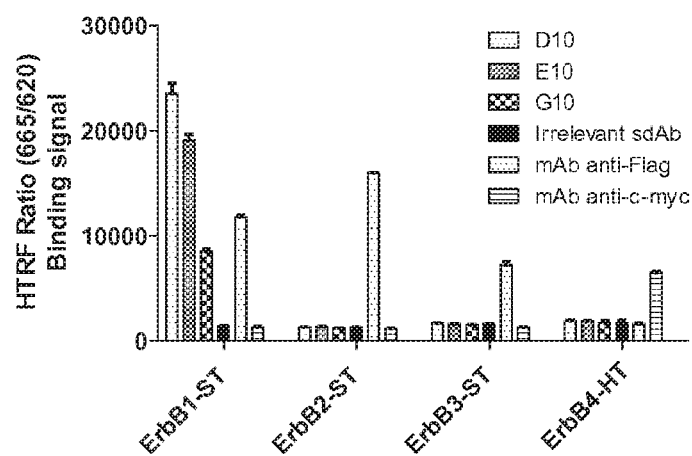
Figure 1D:
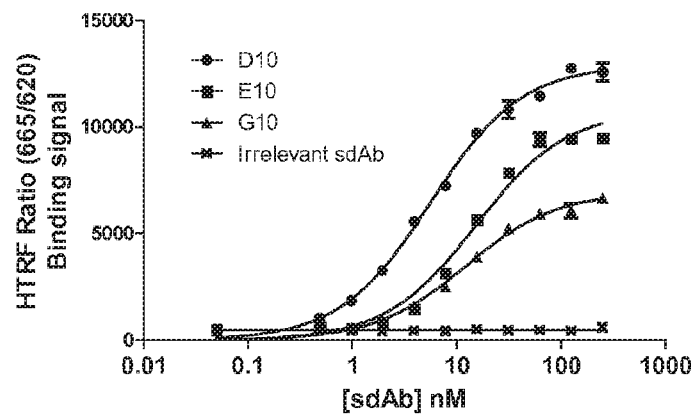

FIG. 1B-D: anti-EGFR sdAb specificity and affinity. B) Specificity of anti-EGFR sdAb D10, E10, G10 on recombinant protein by ELISA. Chimeric ErbB family protein fused to a human Fc fragment were absorbed on plastic plate. SdAb binding was detected using a mouse anti-His mAb followed by a goat anti-mouse-HRP. An anti-Fc mAb was used as a positive control. C) Specificity of anti-EGFR sdAb on transfected HEK 293T cells by HTRF. HEK293T cells were transfected with plasmid ErbB1-ST (SNAP-Tag), ErbB2-ST, ErbB3-ST, ErbB4-HT (HALO-Tag). Each ErbB family receptor were covalently labeled with a donor fluorochrome via their ST or HT. SdAb were incubated with transfected cells and detected using anti-His-d2 (Acceptor). FRET signal represented by the normalized ratio (665/620) indicated an energy transfer between receptor and anti-His-d2. To quantify ErbB receptor expression, a mouse anti-Flag mAb or a anti-c-myc mAb were used to detect ErbB1, 2, 3-ST and ErbB4-HT, respectively D) Affinity of anti-EGFR antibodies on transfected HEK 293T cells determined by HTRF. HEK 293T cells were transfected with plasmid ErbB1-ST and labeled by donor fluorophore. Various concentrations of sdAbs were incubated with cells and detected using acceptor-labeled anti-6His mAb. Apparent Kd were determined by GraphPad. Standard deviations represent three different experiments performed in triplicate.

Figure 2:
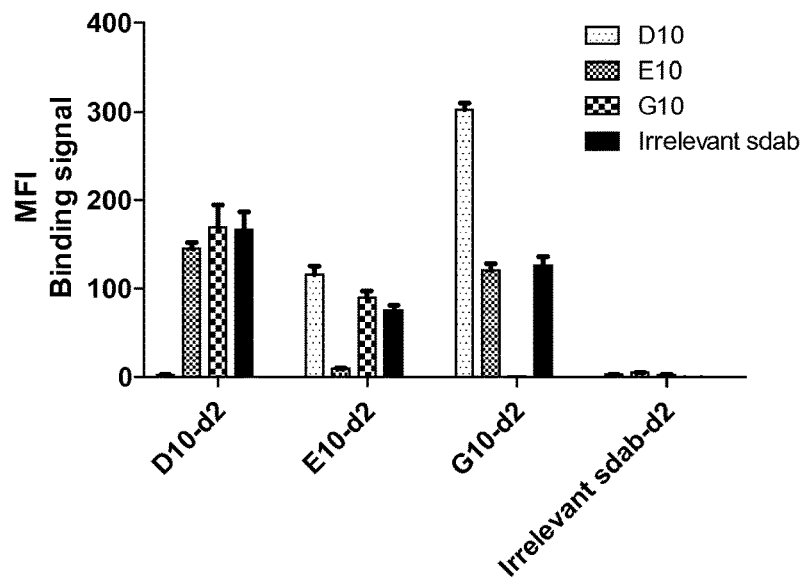
Figure 2:
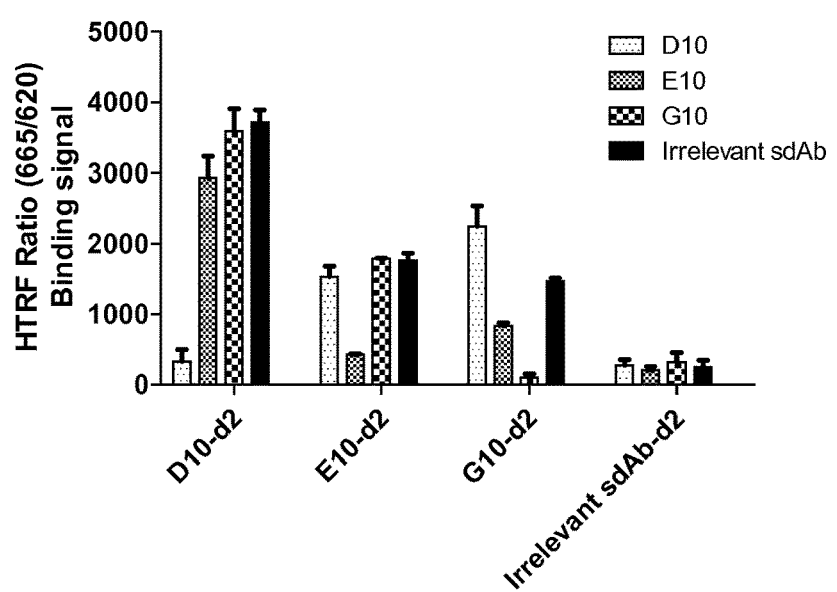

FIG. 2: Competition between anti-EGFR sdAb D10 E10 G10. A) Competition of 3 anti-EGFR sdAbs by flow cytometry. Unlabeled sdAb and d2-labeled sdAbs were incubated together with A431 cells during 2 hours, washed and analyzed on a flow cytometer B) Competition of the sdAbs performed by HTRF. Cells and sdAbs were incubated during 2 hours before reading. In both experiments, unlabeled sdAbs were added using a 1000-fold molar excess, and an irrelevant anti-ErbB2 sdAb was used as negative control. Standard deviations represent three different experiments performed in triplicate.

Figure 3:
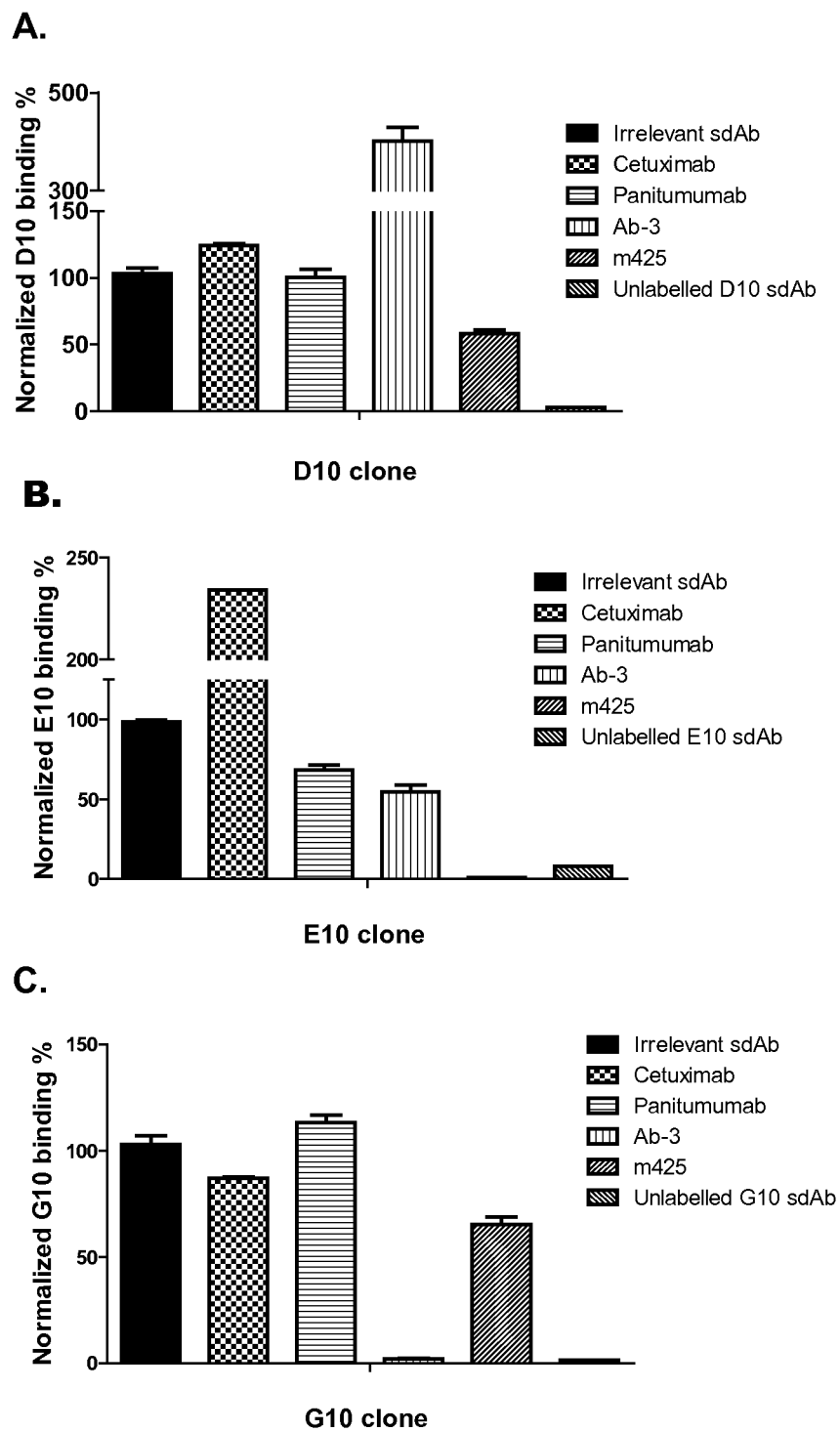

FIG. 3 Competition between sdAbs and reference/therapeutic mAbs by flow cytometry. A) B) and C) represent the competition of d2-labeled sdAbs D10, E10 and G10 respectively. Cetuximab and panitumumab are both anti-ligand domain3 binding site. M425 is the murine parental clone of matuzumab, binding domain III, outside the EFG binding region (this antibodies act like a negative allosteric modulator for ligand binding). Ab-3 (clone EGFR.1) binds EGFR domainI/II. Unlabelled sdAb were used as positive control. Negative control was performed by adding an irrelevant sdAb (anti-ErbB2) as competitor. Labeled-sdAbs and a large excess of mAb were incubated 2 hours at 4° C. before washing and detection. Standard deviations represent three different experiments performed in triplicate.

Figure 4:
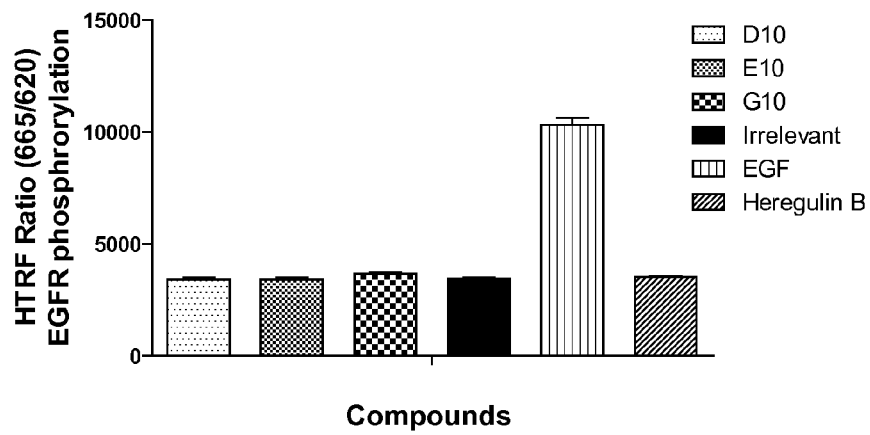
Figure 4:
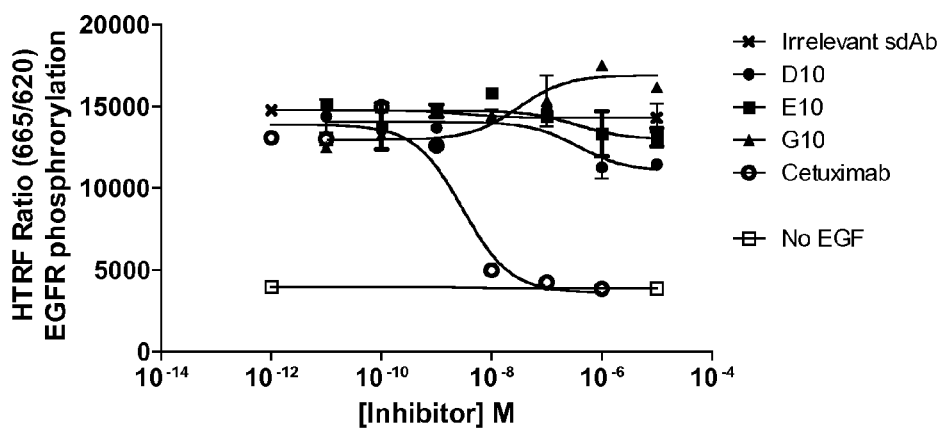
Figure 4:
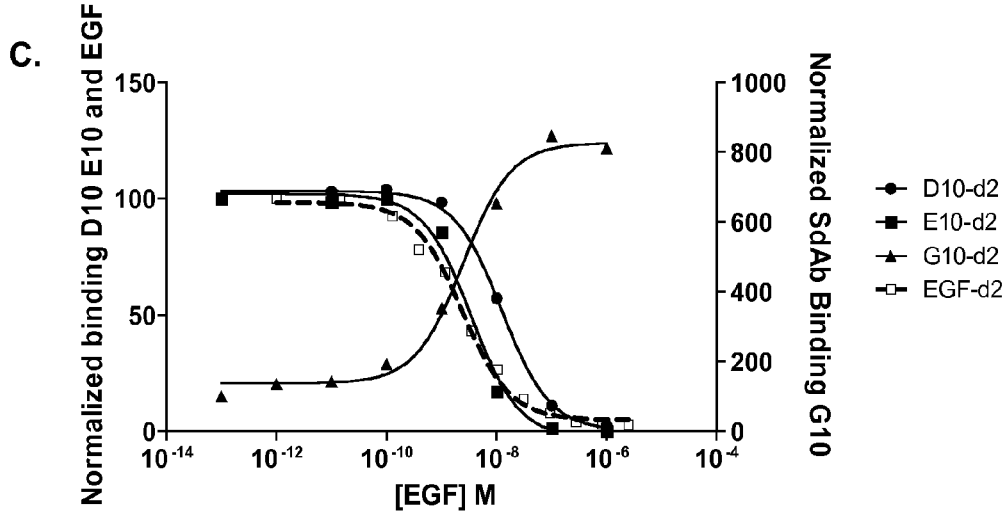

FIG. 4: Competition with Ligand and phosphorylation assays. A) EGFR phosphorylation assays performed using the Phospho-EGFR Kit (Cisbio assays) on A431 cells. Cells were stimulated by 1.5 µM ligand or sdAb during 10 min at room temperature and lysed. EGFR phosphorylation was detected using antibodies anti-EGFR-Tb (donor) and anti-phospho-d2 (acceptor). Energy transfer was measured after an overnight incubation. EGF was used to induce EGFR phosphorylation (positive control), irrelevant sdAb (anti-ErbB3) and heregulin (ErbB3 ligand, does not bind EGFR) were used as negative controls. B) Phosphorylation of EGFR stimulated by EGF (100 nM) in the presence or absence of different antibodies. Maximal phosphorylation was measured upon addition of an irrelevant sdAb (negative competition control). Cetuximab inhibits the EGFR phosphorylation by blocking the ligand binding site.

C) Competition of anti-EGFR sdAbs in the presence of EGF on A431 cells by flow cytometry. The graph was split in two parts, with a left y-axis corresponding to the normalized binding of D10-d2, E10-d2 and EGF-d2, and a right y-axis corresponding to normalized binding of G10-d2. EGF-d2 was used as a positive control for competition. Standard deviations represent three different experiments performed in triplicate.

Figure 5:
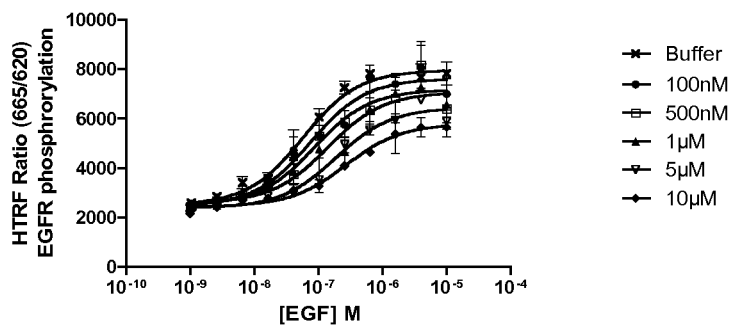
Figure 5:
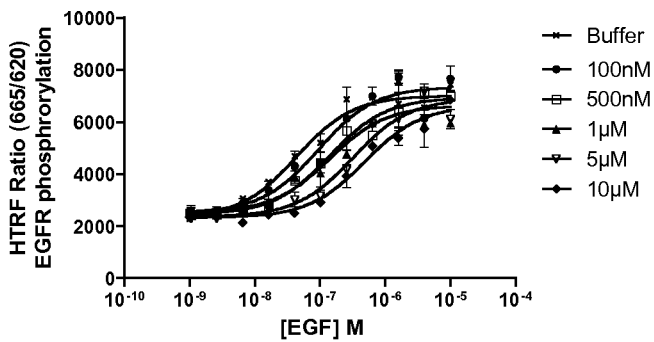
Figure 5:
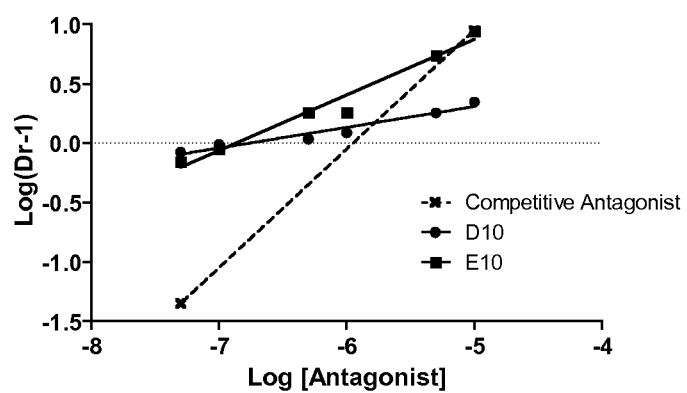

FIG. 5: Schild plot analysis. A) Phosphorylation of EGFR on A431 cells, using various concentrations of EGF in the presence of 5 different concentrations of D10. EGFR phosphorylation was measured using the EGFR phosphorylation kit (Cisbio Bioassays)

B) Phosphorylation of EGFR on A431 cells, using various concentrations of EGF in the presence of 5 different concentrations of E10. C) Schild plot analysis of EGFR phosphorylation in the presence of D10 and E10. HTRF ratios were plotted as a regression of log (dose ratio −1) versus log of molar concentrations of the antagonist (sdAbs). The slopes of resulting lines diverge from 1 (dotted line), indicating that both sdAbs are not competitive antagonists. The calculated slope values are 0.1745 (±0.02082) and 0.4678 (±0.04212) for D10 and E10, respectively. Standard deviations represent three different experiments performed in triplicate.

FIG. 6: EGFR biosensor using anti-EGFR sdAbs by HTRF

A) Cartoon representation of the biosensor experiments using energy transfer. A) EGFR expressed on cells is covalently labeled with donor fluorochrome. A sdAb-d2 (acceptor) is added to cells, leading to energy transfer. Upon EGF ligand addition, EGFR is activated and a major conformational change occurs form tethered (inactivated) to an extended (activated) conformational unfavorable to sdAb binding. After a subsequent addition of an excess of cetuximab blocking the ligand binding site EGFR recovers its inactive conformation, allowing the rebinding of the sdAb-d2. B) Binding of D10-d2 (100 nM) or irrelevant-d2 clone (anti-ErbB2, 100 nM) on EGFR-ST-Tb (Snap tag labeled with terbium), in the presence of increasing concentration of EGF. Irrelevant sdAb-d2 and Heregulin (HRG) were used as a negative control. FRET signals were measured for figure B) C) D) after 1 h of incubation with ligand at 4° C. After this incubation, a 1 µM concentration of cetuximab was added in wells and FRET signals were measured for figure E) F) G) after 2 h incubation. Experiments were performed with 100 nM of D10-d2 (B and E), 100 nM for E10-d2 (C and F) and 4 nM for G10-d2 (D and G).

FIG. 7: Conformational biosensors reveal tethered EGFR involved in EGFR/ErbB2 predimers A) Cartoon depicting the use of anti-EGFR sdAbs as biosensors on EGFR/ErbB2 predimer. B) Affinity of D10 E10 G10 on EGFR/ErbB2 heterodimers. HEK 293T cells were transfected with wild type ErbB1 and ErbB2-ST. Donor fluorochrome were covalently labeled on ErbB2 receptor. D2-labeled sdAbs were added at various concentrations, leading to a FRET signal restricted to heterdimers C) Anti-EGFR sdAb affinity on EGFR/ErbB2 heterodimers in the presence of 500 nM EGF. D-E) Affinity of d2 labeled sdAbs D10, E10, and G10 on NIH/3T3 cells co-transfected with wild type ErbB2 and wild type EGFR. A donor fluorochrome was coupled to an anti-ErbB2 mAb (E2777 clone). The FRET signal was measured after 2 hours of incubation at 4° C. with (E) or without (D) EGF. F) EGFR conformational rearrangement followed by sdAb biosensors on wild type EGFR/ErbB2 heterodimers in the presence of increasing concentrations of EGF. The energy transfer between terbium labeled anti-ErbB2 mAb and anti-His-d2 (acceptor) detecting bound anti-EGFR sdAbs was used to monitor the EGF-induced conformational change of EGFR.

Figure 8:
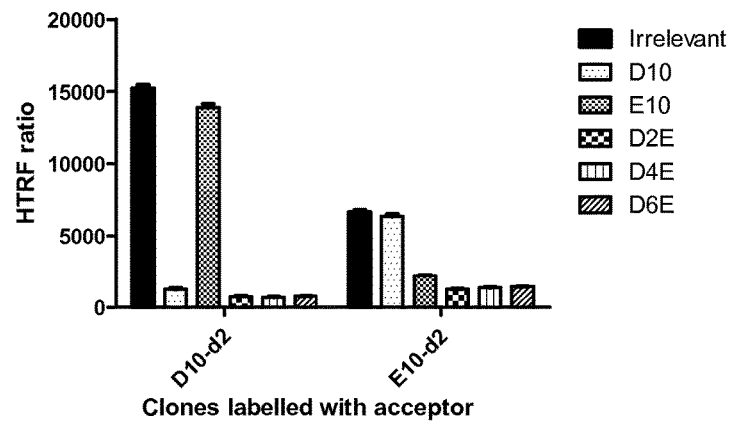

FIG. 8: Competition between labeled monovalent sdAbs and biparatopic antibodies.

Figure 9:
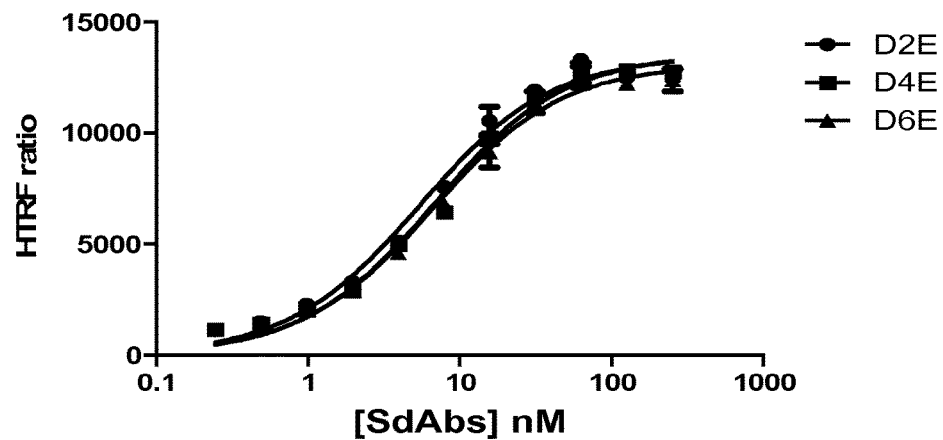
Figure 12:
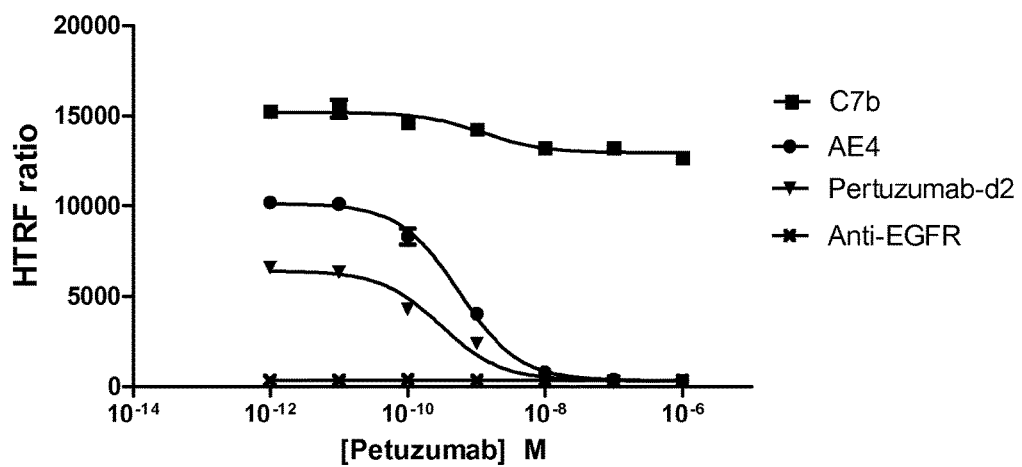
Figure 13:
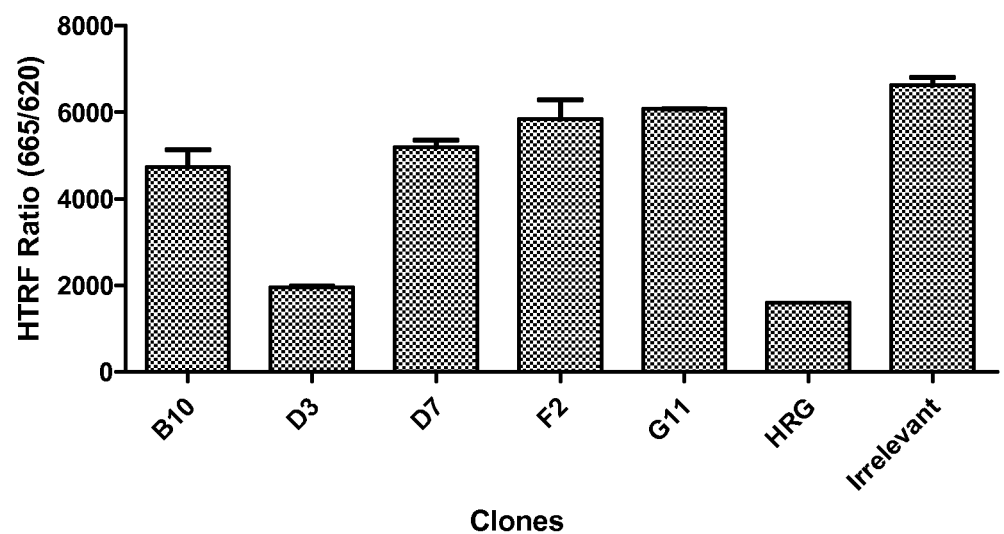

FIG. 9: Apparent affinity of anti-EGFR biparatopic antibodies on living cells FIG. 10: Affinity of anti-EGFR biparatopic sdAb D4E on living cells in competition with monovalent sdAbs FIG. 11: EGFR Phosphorylation induced by ligand in competition with different inhibitors FIG. 12: HTRF competition experiment FIG. 13: HTRF ratio of several clones EXAMPLE 1: CONFORMATIONAL SINGLE DOMAIN ANTIBODIES REVEAL TETHERED EGF RECEPTOR INVOLVED IN EGFR/ERBB2 PREDIMERS Material & Methods Llama Immunization and Library Construction Three llamas (*Lama glama*) were immunized subcutaneously 4 times with 100 µg of recombinant human EGFR/Fc chimera (344ER, R&D Systems), human ErbB2/Fc Chimera (1129-ER, R&D Systems) and human ErbB3/Fc Chimera (348-RB, R&D Systems). VHH library constructions were performed in *E. coli* TG1 strain as previously described in (46, 47). Library diversities were above $10^8$ transformants.

Selection of Single Domain Antibodies by Phage Display

20 µL of the bacteria library was grown in 50 mL of 2YTAG (2YT/Ampicillin (100 µg/mL)/2% Glucose) at 37° C. with shaking (250 rpm) to an OD600 between 0.5 to 0.7. Bacteria were infected by KM13 helper phage using a multiplicity of infection of 20, during 30 min at 37° C. without shaking. The culture was centrifuged for 15 min at 3000 g, and bacterial pellet was resuspended in 250 mL of 2YTA/kanamycine (50 µg/mL) for an overnight phage-sdAb production at 30° C. with shaking. The overnight culture was split in 10 vials and centrifuged for 20 min at 3000 g. Five mL of 80% PEG8000, 2.5 mM NaCl were added to the supernatant in a new clean vial and incubated for 1 h on ice to induce phage particle precipitation. The solution was centrifuged for 20 min at 3000 g at 4° C. and the phage-containing pellet were re-suspended in 1 mL of PBS. Another centrifugation step (2 min, 14000 g) was performed to eliminate bacterial contaminant and 2004 of PEG8000 NaCl was added to supernatants in a new vial. After 30 min on ice and a last centrifugation (5 min, 14000 g), phage-containing pellet were re-suspended in 1 mL PBS to obtain a ready to used Phage-sdAb for selections.

To obtain EGFR specific clones, a first round of selection was performed on magnetic Epoxybeads (Dynabeads, invitrogen) coated with EGFR-Fc during 48 h at 4° C. following recommendations of the manufacturer. Before selection on EGFR-Fc/Epoxybeads, phage-sdAb library was depleted by incubation with ErbB2-Fc/Epoxybeads to eliminate anti-Fc, anti-ErbB2 antibodies, and to reduce non-specific binding. Remaining Phages and EGFR-coated beads were saturated with 2% milk/PBS during 1 h at 4° C., and then phages and antigen were incubated together during 2 h at 4° C. for selection with shaking. Beads were washed 5 times with 1 mL 0.1% Tween PBS and 5 times with PBS. Bound phages were eluted by 1 mg/mL Trypsine solution (Sigma) during 30 min at room temperature with shaking. Phages were rescued and reamplified by infection of TG1 and phage production as above, yielding S1 polyclonal phage population.

To avoid selection against Fc domain and to select antibodies against wild type EGFR, a second round of selection (S2) was performed on A431 cell line ($2 \times 10^7$ cells). S1 Polyclonal phage population and cells were saturated in 2% milk/PBS during 1 h at 4° C., and incubated together in same condition than described previously. After 5 PBS washes, bound phages were eluted using trypsin solution (1 mg/mL) during 30 min at room temperature. Phages were rescued in TG1 and infected bacteria corresponding to S2 were plated. Individual TG1 colonies from S2 were picked and grown in two different 96-deep-well plates in 400 µL of 2YTAG. After overnight growth, half of the culture was frozen at −80° C. in 20% glycerol for backup, and the rest of culture was used for soluble sdAb production induced by isopropyl-β-D- thiogalactopyranoside (IPTG). SdAb concentrations in supernatant were estimated at 100-500 nM using the DoubleTag check kit (Cisbio Bioassays).

Production and Purification of sdAb

For large scale sdAb production, positive phagemids from screening step were transformed in *E. Coli* BL21DE3 strain. Transformed bacteria were grown in 400 mL of 2YTA until OD600=0.7 and induced with 100 µM IPTG for an overnight growth at 30° C. with shaking. The bacteria were pelleted and lysed by freeze-thawing and Bugbuster™ Protein Extraction Reagent (Novagen). After Centrifugation step (3000 g, 20 min), sdAbs were purified from the supernatant using metal affinity chromatography TALON® Superflow™ (GE Healthcare) according to the manufacturer's instructions (48).

Flow Cytometry Experiments

All flow cytometry experiments were performed at 4° C. and in 96 well plates using $2 \times 10^5$ cells/well. Cells were saturated by PBS/2% BSA solution during 1 h with shaking to avoid non specific binding. For screening, 75 µL of sdAb-containing supernatant were added on 75 µl saturated cells and incubated for 1 h. After three washes in PBS/2% BSA, cells were incubated for 1 h with 1/500 anti-6HIS antibody (Novagen), washed 3 times with PBS/2% BSA, and incubated for 1 h with 1/200 PE-conjugated Goat anti mouse antibody (SantaCruz). After three last washes in PBS, fluorescence was measured using a MACSQuant cytometer (Miltenyi) and results were analyzed with the MACSQuant software.

For binding and competition experiments on purified fluorochrome-labeled sdAbs, 75 µL of competitors (therapeutic mAb antibodies, sdAbs or ligands in very large excess) were added to saturated cells with 75 µL of purified labeled-sdAbs diluted in 2% BSA/PBS. After 2 hours at 4° C. with shaking, cells were washed 3 times in PBS and fluorescence was measured on cytometer.

Time Resolved Fluorescence Resonance Energy Transfer (TR-FRET) Assays

HTRF® (Homogenous Time Resolved Fluorescence) combines standard FRET technology with time-resolved measurement of fluorescence (TR-FRET), allowing elimination of short-lived background fluorescence. In this study, HTRF assays were used for binding and competition experiments. All experiments were performed on white 384sv wells plates (Corning) and read on TECAN Infinite M1000. ErbB-SNAPTag plasmids (ErbB-ST, Cisbio bioassays) were FLAG Tagged, and the ErbB4-HALOTag construction (ErbB4-HT, Cisbio bioassays) was c-myc tagged. SNAPTag-fused ErbB family receptors are totally active, and present the same pharmacology than WT receptors (Validated by Cisbio Bioassays).

Binding assays were performed using HEK-293T cells transfected with ErbB-ST and HT receptors. After a 24 h transfection with Lipofectamine 2000 (Invitrogen) following the constructor's recommendation, adherent cells were washed with pre-warmed TagLite buffer. Cells were incubated with 100 nM SNAP-Tb (Donor fluorochrome from Cisbio Biossays) for 1 h at 37° C. During this step, Tb criptate fluorochrome was covalently coupled to ErbB receptors via the SNAPTag fusion. Cells were washed 4 times directly on flasks using TagLite buffer, and were detached from their support using Accutase solution (Thermo). After 2 final TagLite washes, 10 µL of ErbB-ST-Tb cells were dispensed on small volume wells with 5000 or 10000 cells/well. SdAbs were incubated with transfected cells and revealed generally by 200 nM anti-His-D2. When using labeled sdAb-d2, anti-His-d2 was replaced by 54 of Taglite buffer. After 2 h incubation at 4° C., d2 acceptor TR-FRET signal (665 nm) and Tb donor signal (620 nm) were measured using a 60 µs delay, and a 400 µs integration upon excitation at 337 nm (on Tecan infinite M1000). HTRF ratio (665 nm/620 nm $\times 10^4$, Cisbio patent U.S. Pat. No. 5,527,684) was calculated for preventing interference due to medium variability, chemical compound or to normalized experiments when using cells expressing different receptors levels.

For competition experiments, competitors were incubated with sdAbs, and fluorescence was measured after waiting for equilibrium (usually 2 h at 4° C.). Datas from HTRF experiments were analyzed by GraphPad.

Enzyme Linked Immunosorbent assay (ELISA)

One hundred µL of ErbB1-Fc, ErbB2-Fc, ErbB3-Fc, ErbB4-Fc chimera proteins (R&D Systems) at 10 µg/mL were incubated in each well on Maxisorp plate (Nunc) during 24 h at 4° C. After proteins absorption, wells were saturated by PBS/2% BSA for 1 h at room temperature, and incubated with 50 µL purified sdAb (2 µg/mL) during 1 h at 4° C. with shaking. Non-bound sdAbs were washed 3 times in PBS/2% BSA. At last, sdAbs were detected using 50 µL 1/5000 Anti-His HRP (Milteniy). After 1 h incubation and three washes with 0.1% Tween PBS, three washes in PBS, bound secondary antibodies were detected using ABTS (2 2'-azino-bis(3-ethylbenzthiazoline-6-sulphonic acid), Sigma). Absorbance was measured at 405 nm on TECAN infinite M1000

Fluorochrome SdAbs Labeling

Purified antibodies were dialyzed during 24 h in a ($PO_4$) 50 mM pH 8 buffer with a 10 kDa cutoff membrane. After dialyze, fluorochrome (Tb-NHS and d2-NHS) and sdAbs were incubated together with a 6 to 1 molarity ratio, during 45 min at room temperature with shaking. After incubation, labeled sdAb were separated by gel filtration chromatography NAP 5/10/25 (GE Healthcare) according to protein quantity. Chromatography columns were equilibrated by 100 mM pH7 phosphate buffer, before loading proteins. Purified samples were eluted from the column with Phosphate buffer and split by 100 µL fractions. For each fraction, a wavelength scan measurement was performed to calculate fluorochrome/sdAb ratio. Fractions with similar RMF (Relative median Fluoresence) were pooled.

Reagent, Cell Lines and Antibodies

HEK293T, A431 and SKOV3 cells were obtained from ATCC. Cells lines were cultivated in DMEM (Invitrogen) complemented with 10% (v/v) Bovine Serum gold (PAA). Cetuximab and panitumumab were a kind gift from Rémy Castellano (CRCM U1068, TrGET plateform: Preclinical trials). All HTRF Reagents, labeled Antibodies, labeled ligand, SNAP-tag Plasmids, were a kind Gift from Cisbio Bioassays.

Results

Selection of sdAbs Displaying High Specificity and Affinity for EGFR

Anti-EGFR sdAbs were isolated from the repertoire of immunized llamas by alternating phages display selections on recombinant EGFR-Human Fc fusion protein and epidermoid carcinoma tumor cell line A431 (29). Three clones D10, E10 and G10, representative of the final outputs and displaying different sequences were chosen, produced and purified for further characterization. Their binding on all ErbB family members was assayed by ELISA on chimeric recombinant proteins (FIG. 1B) and on Homogenous-Time Resolved Fluorescence (HTRF) on transfected cells (FIG. 1C) to confirm their specificity. ELISA experiments demonstrated that all sdAbs clones were highly specific to EGFR. The same result was obtained using a HTRF assay on HEK293T cells transfected with ErbB family receptors fused to the Snap tag (ST) or Halo tag (HT) (30-32), confirming their ability to bind their antigen in the cell membrane context (FIG. 1C). D2-labeled anti-tag monoclonal antibodies (mAbs) (FLAG-d2 or c-myc-d2) were used to control the membrane expression of all receptors.

The apparent affinity of the anti-EGFR sdAbs for their target was measured by Time resolved fluorescence using living cells. The measured affinities of sdAbs for EGFR-ST transfected HEK293T cells were 7 nM, 25 nM and 15 nM for D10, E10 and G10 respectively (FIG. 1D). In this experiment, sdAbs were detected using an anti-His tag-d2 antibody. To avoid the possible influence of the detection antibody on the dissociation constant measurement, sdAbs were directly coupled with a fluorochrome, and affinity experiments were performed in the same conditions (Table 1). Surprisingly, D10-d2, E10-d2 and G10-d2 displayed slightly higher apparent $K_D$ of 27 nM, 106 nM and 87 nM respectively. These small discrepancies could be explained by a partial denaturation of the sdAbs due to the modification of lysine residues by the NHS-d2 fluorochrome. Nevertheless, both approaches confirmed that these monovalent binders could bind their target with high affinity.

Anti-EGFR sdAbs Target 3 Distinct Epitopes and do not Bind the Ligand Binding Site Although the anti-EGFR sdAbs displayed very different variable CDRs (FIG. 1A), they did not necessarily bind distinct epitopes. To establish this fact, competition experiments were performed using labeled sdAds and unlabeled antibodies using flow cytometry (FIG. 2A) and HTRF (FIG. 2B) experiments. In both techniques, all three sdAb-d2 did compete with themselves (as unlabeled sdAb) but did not compete with the two other sdAbs, demonstrating that 3 distinct EGFR epitopes are recognized by these 3 sdAbs. The apparent affinities of each sdAb were determined again in the presence of the other sdAbs (Table 2). Interestingly, the apparent affinity of G10-d2 for EGFR slightly increased in the presence of D10, but D10-d2 affinity was unaffected by the presence of G10.

Anti-EGFR sdAbs Target 3 Distinct Epitopes and Do Not Bind the Ligand Binding Site Although the anti-EGFR sdAbs displayed very different variable CDRs (FIG. S1), they did not necessarily bind distinct epitopes. To establish this fact, competition experiments were performed using labeled sdAds and unlabeled antibodies using flow cytometry (FIG. 2A) and HTRF (FIG. 2B) experiments. In both techniques, all three sdAb-d2 did compete with themselves (as unlabeled sdAb) but did not compete with the two other sdAbs, demonstrating that 3 distinct EGFR epitopes are recognized by these 3 sdAbs. The apparent affinities of each sdAb were determined again in the presence of the other sdAbs (Table 2). Interestingly, the apparent affinity of G10-d2 for EGFR slightly increased in the presence of D10, but D10-d2 affinity was unaffected by the presence of G10.

In an effort to localize more precisely these three different epitopes, we performed similar competitions experiments using four well characterized anti-EGFR mAbs (cetuximab, panitumumab, Ab-3 and m425). FIG. 3 shows results obtained by flow cytometry on A431 cells. D10 did not compete efficiently with any of these mAbs. Conversely, the binding of Ab-3 (anti-domain I/II, Clone EGFR1, (33)) strongly improved the binding of D10. E10 binding was totally abrogated in the presence of m425 (anti-domain III, murine parental clone of matuzumab (34)) but increased by a factor two in the presence of cetuximab (targeting the ligand binding site on domain III (35)). These results suggest that E10 bind EGFR domain 3 away from the ligand binding site. Ab-3 efficiently competed with G10 suggesting that the epitope of this sdAb is located on domain I/II of EGFR. Finally, the presence of cetuximab and panitumumab did not hinder the binding of the three sdAbs suggesting that none of them is binding the EGFR ligand binding site.

Binding of EGFR to its ligand has a major effect on sdAb binding.

Next, we investigated direct and indirect effects between ligand binding and sdAb binding. First, we checked whether the binding of sdAbs in the absence of ligand could have an influence on the phosphorylation of EGFR intracellular domain. Cells were incubated with saturating concentrations of sdAbs (1.5 µM for 10 min) and the phosphorylation status of EGFR was followed using an EGFR phosphorylation kit (Cisbio). Epidermal growth factor (EGF) and heregulin (ErbB3 ligand) were used as a positive control and negative control respectively. FIG. 4A shows that under these conditions, and unlike EGF, sdAbs are not capable of directly triggering EGFR phosphorylation.

A direct effect on EGFR phosphorylation being excluded, we designed an HTRF competition experiment to determine if the sdAbs could influence the ligand-induced phosphorylation (FIG. 4B). Cetuximab, an EGFR ligand binding site blocking antibody, was used as a positive control for inhibition. As expected, as low as 10 nM cetuximab could totally inhibit the EGF-induced phosphorylation by direct competition with EGF. In contrast, only a slight reduction of the EGFR phosphorylation (20%) could be measured using micromolar concentrations of D10 and E10. Interestingly, G10 led to a slight increase of EGF-induced phosphorylation efficiency, thereby acting as a weak positive allosteric modulator (PAM) (FIG. 4B).

It is well known that upon ligand binding, EGFR undergoes major conformational rearrangements. Thus, we investigated the influence of the presence of EGF on the binding efficiencies of anti-EGFR sdAbs by flow cytometry (FIG. 4C). The presence of EGF increased the affinity of G10 by a factor 8, suggesting that G10 preferentially binds the extended conformation of EGFR, and clearly confirming that G10 does not bind to the EGFR ligand binding site. This result is also in line with its ability to act as a PAM by stabilizing the extended conformation of EGFR upon binding. Conversely, no binding of D10 and E10 to EGFR could be measured in the presence of an excess of ligand. An inverse correlation could be established between the EGF concentration and sdAb binding efficiency, similar to a direct competition between d2-labeled and unlabeled EGF performed as control (FIG. 4C). Together with the competition experiments with ligand binding site mAbs, these results suggest that D10 and E10 have an exquisite specificity for the tethered (inactive) conformation of EGFR, and cannot bind to the extended conformation triggered by EGF binding.

EGF, D10 and E10 have Three Distinct Epitopes.

To strengthen this hypothesis and confirm that D10 and E10 do not directly compete for binding with EGF, we performed a Schild plot analysis by following EGFR phosphorylation in the presence of increasing concentration of EGF and sdAbs (FIGS. 5A and 5B). By gradually increasing D10 concentrations, we could observe a gradual decrease in the maximal EGFR phosphorylation, but the half maximal effective concentration (EC50) of EGF remained unchanged. On the contrary, using E10 as competitor, we observed a roughly similar maximal phosphorylation and EC50 values increasing with the concentration of E10.

Despite these differences, the Schild plot analysis (FIG. 5C) clearly demonstrates that both sdAbs behave as negative allosteric modulators (NAM). Indeed, slopes obtained using this analysis (0.17 and 0.45 for D10 and E10, respectively) is far from a slope equal to 1 that is expected by a competitive antagonist. Thus, these data confirm that E10 and D10 do not bind to the ligand binding site but instead behave as negative allosteric modulators by stabilizing the inactive (tethered) conformation of EGFR upon binding.

SdAbs as EGFR Biosensors

Figure 6A:
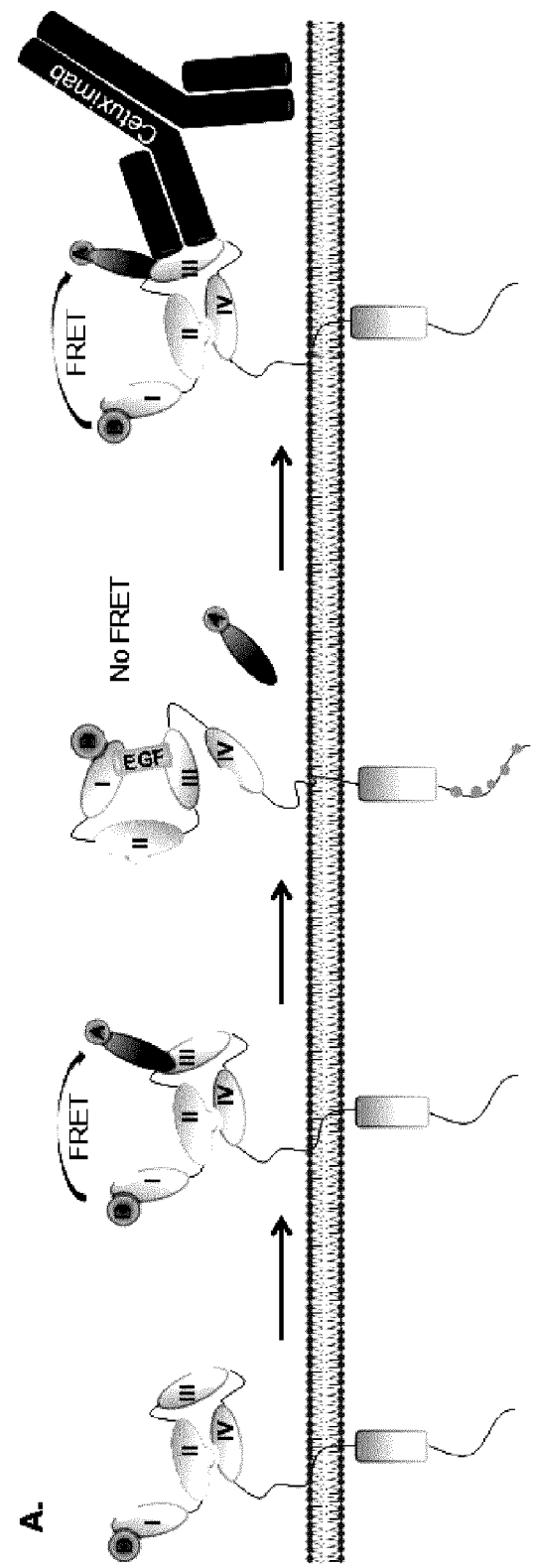

EGFR binders with exquisite specificity for the tethered conformation (D10, E10) or with a strong preference for its extended form (G10) could be powerful tools to directly visualize the EGFR conformation on cells. To explore this possibility, we performed a model experiment using cells transfected with EGFR-ST site-specifically labeled with a terbium donor fluorochrome. In this experiment, we followed the activation of EGFR due to the addition of EGF and its subsequent inactivation due the addition of cetuximab using our conformational probes labeled with an acceptor fluorochrome (d2) (FIG. 6A). Controls were performed using an irrelevant sdAb coupled to d2 fluorochrome, and heregulin as irrelevant ligand. A concentration of 100 nM of D10-d2 and E10-d2 were used to get a high specific signal, while avoiding the NAM effect on EGF binding, negligible at this concentration (FIG. 5).

Figures 6B, 6C, 6D, 6E, 6F, 6G:
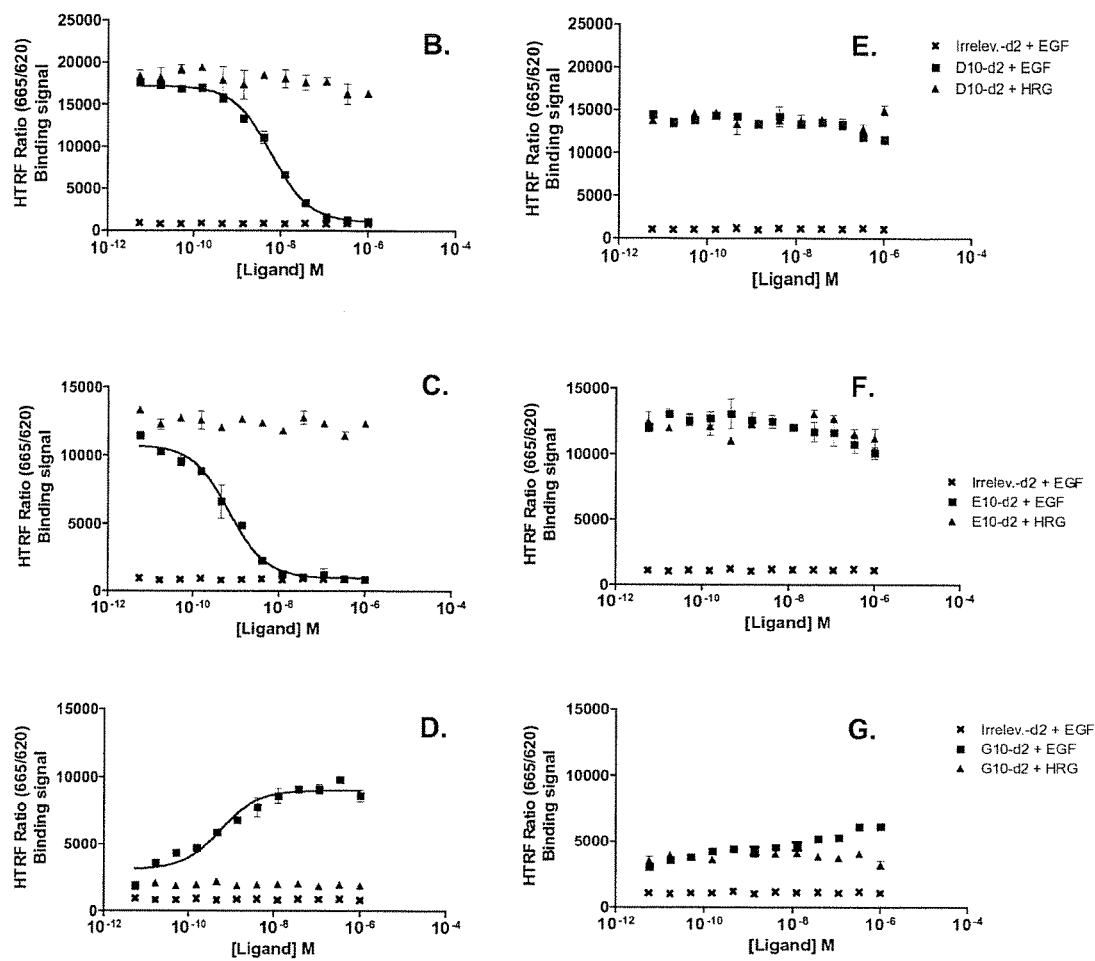

As expected, D10-d2 and E10-d2 binding yielded a high FRET signal that decreased in a dose sensitive fashion upon addition of EGF, thereby directly visualizing the EGFR conformational change (FIGS. 6B and 6C). Strikingly, the simple addition of cetuximab to the mixture could fully restore the FRET signal by competing out the ligand, thereby switching EGFR to its original tethered conformation (FIGS. 6E and 6F). Conversely, G10-d2 used at low concentrations (4 nM) yielded a faint signal in the absence of EGF, which increased in a dose dependent fashion upon addition of EGF, visualizing the apparition of the extended form of EGFR (FIG. 6D). As in the previous experiment, the subsequent addition of cetuximab reestablished the tethered EGFR conformation, thereby drastically reducing the FRET signal (FIG. 6G). Altogether, these results demonstrated that these anti-EGFR sdAbs could be used as sensors of "activated/extended" and "inactivated/tethered" conformation of EGFR.

Conformational Biosensors Reveal Tethered EGFR Involved in EGFR/ErbB2 Predimers.

We finally took advantage of these innovative tools to study the conformation of EGFR involved in a heterodimer such as EGFR/ErbB2, in the presence or absence of ligand.

Figure 7A:
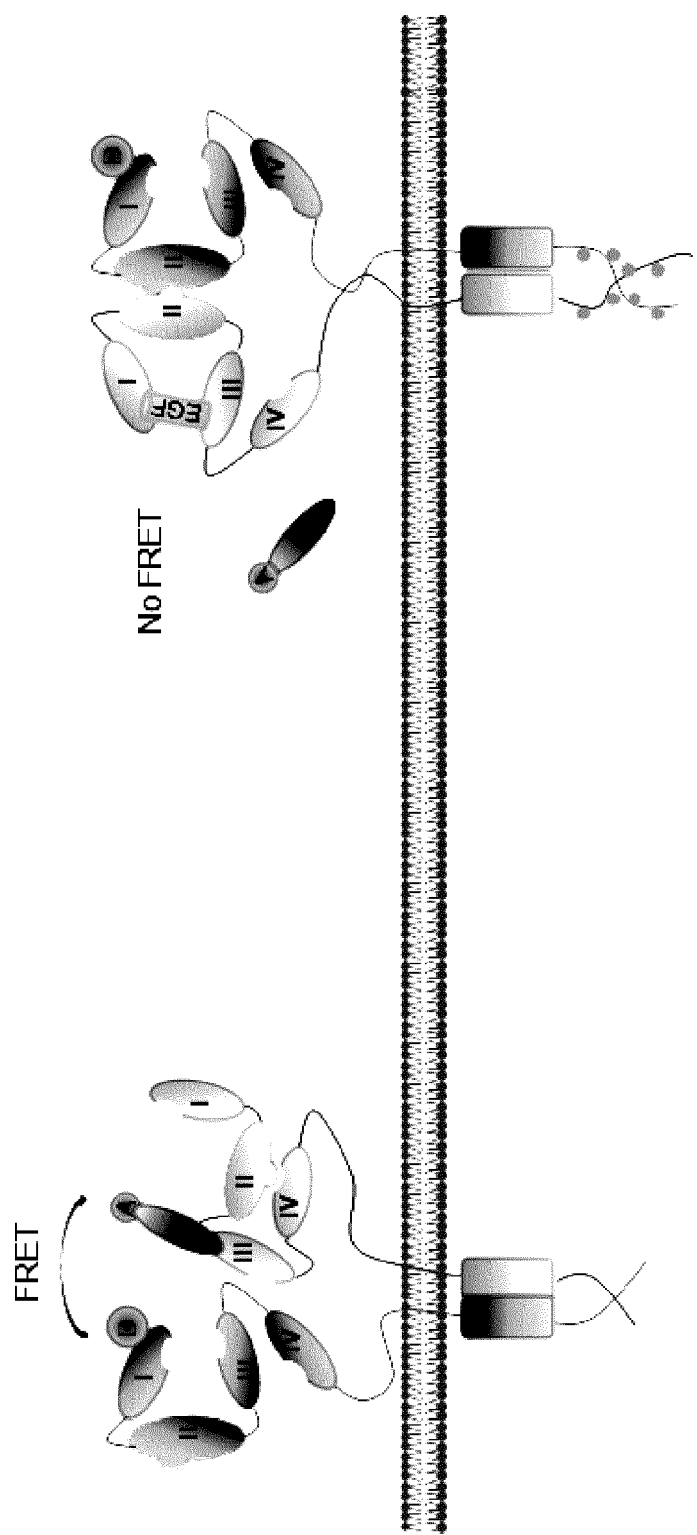
Figures 7B, 7C, 7D, 7E, 7F:
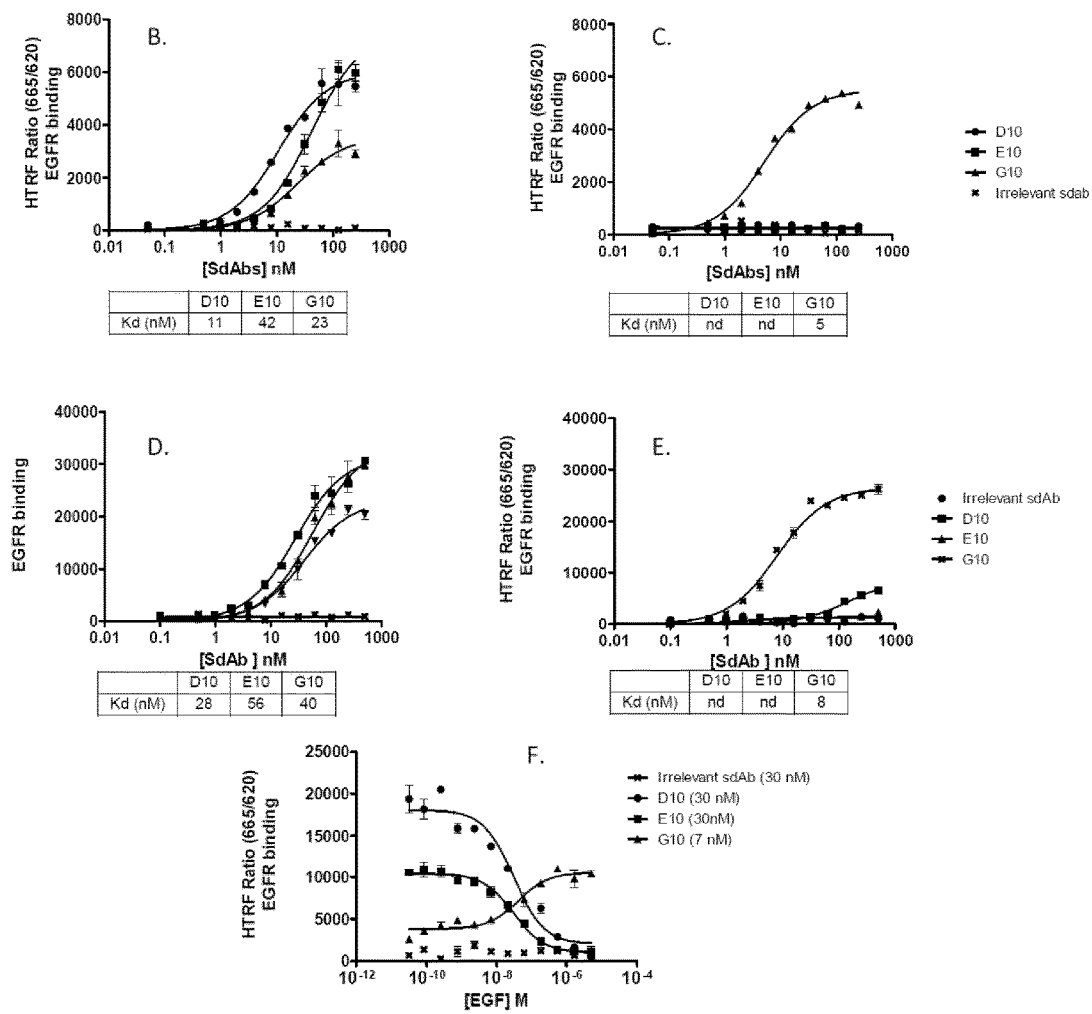

For this purpose, we followed the transfer of fluorescence between a fluorescently tagged ErbB2-ST fusion acting as a donor and acceptor-labeled sdAbs bound to a wild type EGFR. In these conditions, a FRET signal can only be measured in the presence of EGFR/ErbB2 heterodimers (FIG. 7A). Strikingly, a strong signal was measured using the three d2-labeled sdAbs in the absence of EGF (FIG. 7B). As expected, upon addition of EGF, the signal obtained using the "tethered conformation" specific sdAbs D10 and E10 was totally abrogated, due to the EGF-induced EGFR conformational change. The presence of EGFR/ErbB2 dimers was still demonstrated since, in contrast with D10-d2 and E10-d2, G10-d2 yielded a much stronger signal owing to its higher affinity for extended EGFR (FIG. 7C).

Altogether, these experiments confirm that EGFR can form heterodimers with ErbB2 in the absence of ligand and directly demonstrate that within these predimers, EGFR adopts an tethered/inactive conformation despite its stable interaction with ErbB2. These results also confirm that most EGFR engaged in predimers switch to the extended/active conformation in the presence of ligand.

To fully establish the biological relevance of this finding, we explored the possibility to detect tethered EGFR engaged in predimers using wild type ErbB receptors. A murine donor-labeled anti-ErbB2 mAb (E2777) was chosen because targeting epitope is different from therapeutic mAbs on ErbB2. As shown in FIG. 7D and 7E, very similar results were obtained, demonstrating that wild type ErbB receptors efficiently form EGFR/ErbB2 heterodimers in the absence of ligand while predominantly adopting a tethered conformation. Interestingly, the proportion of tethered and extended EGFR varied according to the concentration of EGF, thereby reproducing the results obtained with EGFR expressed in the absence of ErbB2.

Discussion:

In this study, using phage display we selected nanobodies against the epidermal growth factor receptor from the repertoire of an immunized llama. Three EGFR specific clones, with no cross reaction with others members of the ErbB family were fully characterized. SdAbs D10, E10 and G10 bind three distinct epitopes of their target with a high affinity (7, 25 and 15 nM respectively). Competition experiments with reference mAbs cetuximab (36), panitumumab (36), Ab-3 (33), m425 (37) demonstrated that none of these sdAds target the ligand binding site despite the fact that two of these sdAbs cannot bind EGFR in the presence of its ligand. Instead, sdAbs D10 and E10 bind EGFR epitopes that are only present in the inactive conformation of this receptor known to undergo major conformational changes upon ligand binding (7, 38, 39). In contrast G10 bind both conformations of the receptor, but with an apparent affinity eight fold higher for the active conformation. These results highlight the caution that should be taken when interpreting the results of competition experiments of two binders. In fact, the stabilization of an alternative conformation of their target can be misinterpreted as a direct steric hindrance effect due to the targeting of a common epitope. Interestingly, despite their strong binding to specific conformation of EGFR, these sdAbs only lead to weak positive (G10) or negative (D10, E10) allosteric modulation of EGF-driven EGFR phosphorylation, qualifying them as sensitive conformational sensors.

Previous data have demonstrated the presence of EGFR pre-dimers on resting cells (20, 40, 41), estimated to represent about 40% of the total population of EGFRs (42). Some studies have suggested that ligand-independent EGFR predimerization is a mechanism allowing the induction of a faster signal transduction when receptors are stimulated with ligand (43, 44). Teramura et al. suggested that monomers of EGFR exist primarily in the tethered state, and that the formation of predimers biases the structure of EGFR toward extended state-like conformations with high association rates to EGF (43), inducing a dynamic conformational change in the predimer that facilitates and accelerates the formation of signaling dimer of EGF/EGFR complexes. Authors argue that large increases in the association rate of EGF to the predimeric binding sites suggest that the conformation resembles the extended form, and that the association of EGF with one of the EGFR molecules in the dimeric sites might an allosteric conformational change in the EGF binding site in the other EGFR molecule, which could explain a positive cooperativity upon EGF binding. This concept is also favored by molecular dynamic simulations performed by Arkhipov et al. (21). These authors performed molecular dynamics on the crystal structure of the two-ligand extracellular dimer after removal of the EGF and obtained an "active-like" conformation, excepted for domain IV showing a bending motion that would favor the formation of symmetric (inactive) kinase dimers (16).

In this study, we demonstrate that in the absence of ligand, EGFR is also engaged in dimers with ErbB2 as pre-heterodimers. However, unlike the situation described above with EGFR pre-homodimers, EGFR displays a conformation very similar to the tethered inactive conformation. Upon EGF stimulation, EGFR adopts the extended conformation allowing the signaling to occur.

While the significance of these discrepancies deserves further studies, this finding has an importance for the design of efficient inhibitors. Indeed, ErbB2 is frequently overexpressed in a variety of cancer, and has a strong capacity to form heterodimers with ErbB3 and EGFR, and with ErbB4 in a lesser extent (45). In such a situation, a very significant part of EGFR is though to be engaged in EGFR/ErbB2 predimers. Our results imply that the most efficient inhibitors would thus be designed to interact with the tethered conformation of EGFR. Finally, while the anti EGFR sdAbs described in this work have an intrinsic value as conformational sensors, they might also be advantageously used for other application, including imaging, targeting or in high throughput screening approaches aiming at identifying new EGFR inhibitors targeting the extracellular portion of the receptor.

TABLE 1

Affinity values of unlabeled and d2-labeled anti-EGFR sdAbs measured by HTRF on EGFR-ST.

| | Kd (nM) | | |
|---|---|---|---|
| | D10 | E10 | G10 |
| Unlabeled clone | 7 | 25 | 15 |
| d2-labeled clone | 27 | 106 | 87 |

TABLE 2

Affinity values of anti-EGFR sdAbs, in the presence of other nanobodies as measured by HTRF (EGFR-ST)

| | | Competitors | | | |
|---|---|---|---|---|---|
| $K_D$ Value (nM) | | Irrelevant sdAb | D10 | E10 | G10 |
| Clones | D10 | 7 | | 11 | 7 |
| | E10 | 20 | 17 | | 17 |
| | G10 | 12 | 6 | 17 | |

TABLE 3

Affinity of anti-EGFR sdAbs in competition with different mAbs

| | | Competitors | | | | |
|---|---|---|---|---|---|---|
| $K_D$ Value (nM) | | Irrelevant sdAb | Cetuximab | Panitumumab | Ab-3 | m425 |
| Clones | D10 | 7 | 10 | 13 | 3 | 14 |
| | E10 | 20 | 11 | 70 | 67 | No binding |
| | G10 | 12 | 21 | 27 | No Binding | 32 |

EXAMPLE 2: ANTI-EGFR BIPARATOPIC SINGLE DOMAIN BASED ANTIBODY

In these experiments, both anti-EGFR sdAbs (D10 and E10) were covalently linked to determine if their NAM effect could lead to a cumulative inhibition of EGFR phosphorylation induced by EGF ligand. Three different molecules biparatopic single domain antibodies (bisdAbs), called D2E, D4E and D6E, were engineered by linking the C-terminal of D10 sdAb to the N-terminal of E10 using peptide linkers corresponding to 2, 4 or 6 ($G_4S$) motif, respectively.

Sequence of D2E:
(SEQ ID NO: 13)
EVQLQESGGGLVQAGGSLRLSCAVSISRTIFSLYAMEWYRQPPGKQRD

LVARIYRSGDTNYADSVKGRFTISRDNAKNTVYLQMNSLKPEDTGVYY

CNSPAQDWPWGQGTQVTVSSAAA<u>GGGGSGGGGS</u>MAQVQLQESGGGLAQ

AGGSLRLSCAASGRTLSSYDMGWFRQAPGKEREFVTAINWGDLSTYYA

DSVKGRFTISRDNAKNTVYLQMNSLKPEDTAVYYCAARLRYTVSDPIF

SRPDRYNYWGQGTQVTVSSAAAEQKLISEEDLNGAAHHHHHHGS

Sequence of D4E:
(SEQ ID NO: 14)
EVQLQESGGGLVQAGGSLRLSCAVSISRTIFSLYAMEWYRQPPGKQRD

LVARIYRSGDTNYADSVKGRFTISRDNAKNTVYLQMNSLKPEDTGVYY

CNSPAQDWPWGQGTQVTVSSAAA<u>GGGGSGGGGSGGGGSGGGGS</u>MAQVQ

LQESGGGLAQAGGSLRLSCAASGRTLSSYDMGWFRQAPGKEREFVTAI

NWGDLSTYYADSVKGRFTISRDNAKNTVYLQMNSLKPEDTAVYYCAAR

LRYTVSDPIFSRPDRYNYWGQGTQVTVSSAAAEQKLISEEDLNGAAHH

HHHHGS

Sequence of D6E:
(SEQ ID NO: 15)
EVQLQESGGGLVQAGGSLRLSCAVSISRTIFSLYAMEWYRQPPGKQRD

LVARIYRSGDTNYADSVKGRFTISRDNAKNTVYLQMNSLKPEDTGVYY

CNSPAQDWPWGQGTQVTVSSAAA<u>GGGGSGGGGSGGGGSGGGGSGGGGS</u>

<u>GGGGS</u>MAQVQLQESGGGLAQAGGSLRLSCAASGRTLSSYDMGWFRQAP

GKEREFVTAINWGDLSTYYADSVKGRFTISRDNAKNTVYLQMNSLKPE

DTAVYYCAARLRYTVSDPIFSRPDRYNYWGQGTQVTVSSAAAEQKLIS

EEDLNGAAHHHHHHGS

After production and purification, competition and affinity experiments were performed to confirm that these molecules still bind EGFR with a strong affinity. Labeled monovalent D10-d2 and E10-d2 sdAbs were used in competition with D2E D4E and D6E (FIG. 8). All bisdAbs fully competed with both sdAbs D10-d2 and E10-D2, implying that both nanobodies of all three bisdAbs were still active.

Figure 10:
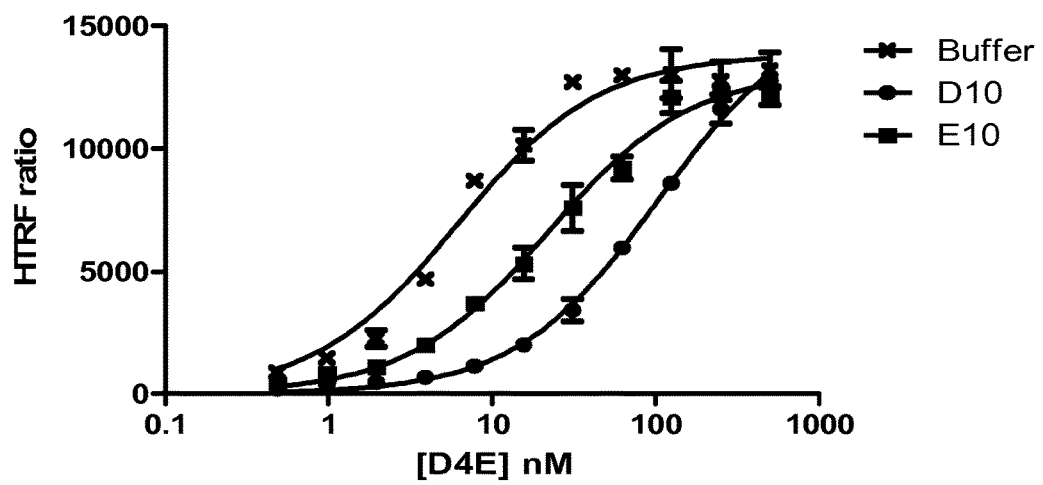

The apparent affinity of the biparatopic molecules for EGFR was measured by time resolved fluorescence using living cells. The measured affinities for biparatopic on EGFR-ST transfected HEK293T cells were obtained for D2E, D4E and D6E. Surprisingly, the size of the linker did not affect the binding properties i.e. same apparent affinities were obtained for these three different molecules (6 nM, FIG. 9). D4E was chosen for further characterization. The apparent affinity of bisdAb D4E in the presence of a large amount of monovalent D10 or E10 was used to estimate the apparent affinity of each sdAb moiety (the epitope of one sdAb moiety being blocked by the excess of corresponding monovalent sdAb) (FIG. 10). Under such conditions, the sdAb D10 moiety of D4E displayed an affinity of 22 nM (compared to 6 nM for the free sdAb) while the sdAb E10 moiety displayed an affinity of 100 nM (FIG. 10). The reduced affinity of the E10 moiety compared to the parental sdAb (25 nM) may be explained by the presence of the peptide linker at its N-terminal extremity, i.e. in close proximity to the paratope of the antibody.

Figure 11:
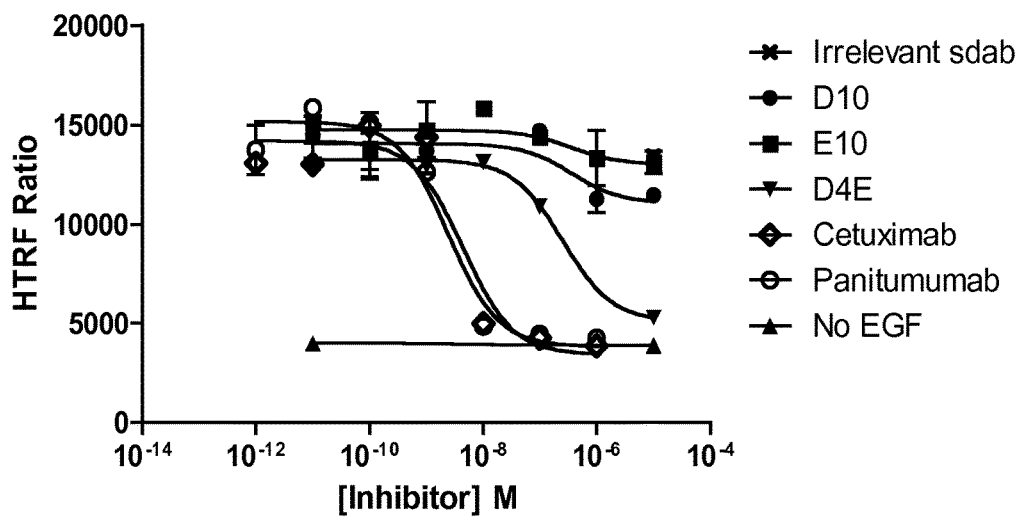

Next, we designed an HTRF competition experiment to study the influence of D4E on ligand-induced phosphorylation (FIG. 11). Cetuximab, a ligand binding site blocking antibody was used as a positive control for inhibition. As expected, as low as 10 nM cetuximab could totally inhibit the EGF-induced phosphorylation by direct competition with EGF. In contrast, only a slight reduction of the EGFR phosphorylation (20%) could be measured using micromolar concentrations of D10 and E10. By contrast, bisdAb D4E could strongly inhibit the EGFR phosphorylation but at concentration 100 fold higher than the one used to observe a similar effect with cetuximab.

Because the bisdAb acts as a negative allosteric modulator and does not interact with the EGF ligand binding site, it does not compete with cetuximab and could be used simultaneously. An anti-EGFR biparatopic nanobody has already been published previously (Roovers, R. C., M. J. Vosjan, T. Laeremans, R. el Khoulati, R. C. de Bruin, K. M. Ferguson, A. J. Verkleij, G. A. van Dongen and P. M. van Bergen en Henegouwen (2011). "A biparatopic anti-EGFR nanobody efficiently inhibits solid tumour growth." Int J Cancer 129(8): 2013-2024) and was shown to inhibit tumor progression in mice. But that molecule was initially designed to compete with therapeutics mAb (cetuximab and matuzumab), thus excluding the possibility to use the molecule in combination with these FDA approved antibodies. In contrast, bisdAb D4E seems to compete with matuzumab but do not compete with cetuximab, thereby offering the possibility to use these two molecules in combination therapy.

REFERENCES

Throughout this application, various references describe the state of the art to which this invention pertains. The disclosures of these references are hereby incorporated by reference into the present disclosure.

1. Oda K, Matsuoka Y, Funahashi A, & Kitano H (2005) A comprehensive pathway map of epidermal growth factor receptor signaling. Molecular systems biology 1:2005 0010.
2. Roskoski R, Jr. (2014) The ErbB/HER family of protein-tyrosine kinases and cancer. Pharmacological research: the official journal of the Italian Pharmacological Society 79:34-74.
3. Lemmon M A (2009) Ligand-induced ErbB receptor dimerization. Experimental cell research 315(4):638-648.
4. Cho H S & Leahy D J (2002) Structure of the extracellular region of HER3 reveals an interdomain tether. Science 297(5585):1330-1333.
5. Ferguson K M, et al. (2003) EGF activates its receptor by removing interactions that autoinhibit ectodomain dimerization. Molecular cell 11(2):507-517.
6. Garrett T P, et al. (2002) Crystal structure of a truncated epidermal growth factor receptor extracellular domain bound to transforming growth factor alpha. Cell 110(6): 763-773.
7. Ogiso H, et al. (2002) Crystal structure of the complex of human epidermal growth factor and receptor extracellular domains. Cell 110(6):775-787.
8. Schlessinger J (2002) Ligand-induced, receptor-mediated dimerization and activation of EGF receptor. Cell 110(6): 669-672.
9. Zhang X, Gureasko J, Shen K, Cole P A, & Kuriyan J (2006) An allosteric mechanism for activation of the kinase domain of epidermal growth factor receptor. Cell 125(6):1137-1149.
10. Moriki T, Maruyama H, & Maruyama I N (2001) Activation of preformed EGF receptor dimers by ligand-induced rotation of the transmembrane domain. Journal of molecular biology 311(5):1011-1026.
11. Junttila T T, et al. (2009) Ligand-independent HER2/HER3/PI3K complex is disrupted by trastuzumab and is effectively inhibited by the PI3K inhibitor GDC-0941. Cancer cell 15(5):429-440.
12. Kawashima N, et al. (2010) Reversible dimerization of EGFR revealed by single-molecule fluorescence imaging using quantum dots. Chemistry 16(4):1186-1192.
13. Gadella T W, Jr. & Jovin T M (1995) Oligomerization of epidermal growth factor receptors on A431 cells studied by time-resolved fluorescence imaging microscopy. A stereochemical model for tyrosine kinase receptor activation. The Journal of cell biology 129(6):1543-1558.
14. Yu X, Sharma K D, Takahashi T, Iwamoto R, & Mekada E (2002) Ligand-independent dimer formation of epidermal growth factor receptor (EGFR) is a step separable from ligand-induced EGFR signaling. Molecular biology of the cell 13(7):2547-2557.
15. Macdonald-Obermann J L, Piwnica-Worms D, & Pike L J (2012) Mechanics of EGF receptor/ErbB2 kinase activation revealed by luciferase fragment complementation imaging. Proceedings of the National Academy of Sciences of the United States of America 109(1):137-142.
16. Jura N, et al. (2009) Mechanism for activation of the EGF receptor catalytic domain by the juxtamembrane segment. Cell 137(7):1293-1307.
17. Endres N F, et al. (2013) Conformational coupling across the plasma membrane in activation of the EGF receptor. Cell 152(3):543-556.
18. Mi L Z, et al. (2011) Simultaneous visualization of the extracellular and cytoplasmic domains of the epidermal growth factor receptor. Nature structural & molecular biology 18(9):984-989.
19. Liu P, et al. (2012) A single ligand is sufficient to activate EGFR dimers. Proceedings of the National Academy of Sciences of the United States of America 109(27):10861-10866.
20. Macdonald-Obermann J L, Adak S, Landgraf R, Piwnica-Worms D, & Pike L J (2013) Dynamic analysis of the epidermal growth factor (EGF) receptor-ErbB2-ErbB3 protein network by luciferase fragment complementation imaging. The Journal of biological chemistry 288(42):30773-30784.
21. Arkhipov A, et al. (2013) Architecture and membrane interactions of the EGF receptor. Cell 152(3):557-569.
22. Muyldermans S (2013) Nanobodies: natural single-domain antibodies. Annual review of biochemistry 82:775-797.

23. Perez J M, et al. (2001) Thermal unfolding of a llama antibody fragment: a two-state reversible process. *Biochemistry* 40(1):74-83.
24. Gueorguieva D, et al. (2006) Identification of single-domain, Bax-specific intrabodies that confer resistance to mammalian cells against oxidative-stress-induced apoptosis. *FASEB journal: official publication of the Federation of American Societies for Experimental Biology* 20(14):2636-2638.
25. Muyldermans S (2001) Single domain camel antibodies: current status. *Journal of biotechnology* 74(4):277-302.
26. De Genst E, et al. (2006) Molecular basis for the preferential cleft recognition by dromedary heavy-chain antibodies. *Proceedings of the National Academy of Sciences of the United States of America* 103(12):4586-4591.
27. Irannejad R, et al. (2013) Conformational biosensors reveal GPCR signalling from endosomes. *Nature* 495 (7442):534-538.
28. Staus D P, et al. (2014) Regulation of beta2-Adrenergic Receptor Function by Conformationally Selective Single-Domain Intrabodies. *Molecular pharmacology* 85(3):472-481.
29. Gaborit N, et al. (2011) Time-resolved fluorescence resonance energy transfer (TR-FRET) to analyze the disruption of EGFR/HER2 dimers: a new method to evaluate the efficiency of targeted therapy using monoclonal antibodies. *The Journal of biological chemistry* 286(13):11337-11345.
30. Juillerat A, et al. (2003) Directed evolution of O6-alkylguanine-DNA alkyltransferase for efficient labeling of fusion proteins with small molecules in vivo. *Chemistry & biology* 10(4):313-317.
31. Gautier A, et al. (2008) An engineered protein tag for multiprotein labeling in living cells. *Chemistry & biology* 15(2):128-136.
32. Los G V, et al. (2008) HaloTag: a novel protein labeling technology for cell imaging and protein analysis. *ACS chemical biology* 3(6):373-382.
33. Cochran J R, Kim Y S, Olsen M J, Bhandari R, & Wittrup K D (2004) Domain-level antibody epitope mapping through yeast surface display of epidermal growth factor receptor fragments. *Journal of immunological methods* 287(1-2):147-158.
34. Rodeck U, et al. (1987) Tumor growth modulation by a monoclonal antibody to the epidermal growth factor receptor: immunologically mediated and effector cell-independent effects. *Cancer research* 47(14):3692-3696.
35. Li S, et al. (2005) Structural basis for inhibition of the epidermal growth factor receptor by cetuximab. *Cancer cell* 7(4):301-311.
36. Voigt M, et al. (2012) Functional dissection of the epidermal growth factor receptor epitopes targeted by panitumumab and cetuximab. *Neoplasia* 14(11):1023-1031.
37. Schmiedel J, Blaukat A, Li S, Knochel T, & Ferguson K M (2008) Matuzumab binding to EGFR prevents the conformational rearrangement required for dimerization. *Cancer cell* 13(4):365-373.
38. Kowal J, et al. (2014) Ligand-induced structural changes in the cyclic nucleotide-modulated potassium channel MloK1. *Nature communications* 5:3106.
39. Remy I, Wilson I A, & Michnick S W (1999) Erythropoietin receptor activation by a ligand-induced conformation change. *Science* 283(5404):990-993.
40. Sako Y, Minoghchi S, & Yanagida T (2000) Single-molecule imaging of EGFR signalling on the surface of living cells. *Nature cell biology* 2(3):168-172.
41. Clayton A H, Orchard S G, Nice E C, Posner R G, & Burgess A W (2008) Predominance of activated EGFR higher-order oligomers on the cell surface. *Growth factors* 26(6):316-324.
42. Holman E G, et al. (2010) Ligand-induced EGF receptor oligomerization is kinase-dependent and enhances internalization. *The Journal of biological chemistry* 285(50): 39481-39489.
43. Teramura Y, et al. (2006) Single-molecule analysis of epidermal growth factor binding on the surface of living cells. *The EMBO journal* 25(18):4215-4222.
44. Chung I, et al. (2010) Spatial control of EGF receptor activation by reversible dimerization on living cells. *Nature* 464(7289):783-787.
45. Holbro T, Civenni G, & Hynes N E (2003) The ErbB receptors and their role in cancer progression. *Experimental cell research* 284(1):99-110.
46. Behar G, et al. (2009) Llama single-domain antibodies directed against nonconventional epitopes of tumor-associated carcinoembryonic antigen absent from nonspecific cross-reacting antigen. *FEBS J* 276(14):3881-3893.
47. Alvarez-Rueda N, et al. (2007) Generation of llama single-domain antibodies against methotrexate, a prototypical hapten. *Mol Immunol* 44(7):1680-1690.
48. Even-Desrumeaux K, Baty D, & Chames P (2010) Strong and oriented immobilization of single domain antibodies from crude bacterial lysates for high-throughput compatible cost-effective antibody array generation. *Mol Biosyst* 6(11):2241-2248.

The invention claimed is:

1. An isolated anti-Epidermal Growth Factor Receptor (EGFR) single domain antibody comprising
   i) a CDR1 having a sequence set forth as SEQ ID NO: 1, a CDR2 having a sequence set forth as SEQ ID NO:2 and a CDR3 having a sequence set forth as SEQ ID NO:3;
   ii) a CDR1 having a sequence set forth as SEQ ID NO:5, a CDR2 having a sequence set forth as SEQ ID NO:6 and a CDR3 having a sequence set forth as SEQ ID NO:7;
   or
   iii) a CDR1 having a sequence set forth as SEQ ID NO:9, a CDR2 having a sequence set forth as SEQ ID NO:10 and a CDR3 having a sequence set forth as SEQ ID NO:11.

2. The isolated single domain antibody of claim 1 which has a sequence set forth as SEQ ID NO:4, SEQ ID NO: 8 or SEQ ID NO: 12.

3. The single domain antibody according to claim 1 which is a humanized single domain antibody.

4. A polypeptide comprising at least one anti-EGFR single domain antibody comprising
   i) a CDR1 having a sequence set forth as SEQ ID NO: 1, a CDR2 having a sequence set forth as SEQ ID NO:2 and a CDR3 having a sequence set forth as SEQ ID NO:3;
   ii) a CDR1 having a sequence set forth as SEQ ID NO:5, a CDR2 having a sequence set forth as SEQ ID NO:6 and a CDR3 having a sequence set forth as SEQ ID NO:7;
   or
   iii) a CDR1 having a sequence set forth as SEQ ID NO:9, a CDR2 having a sequence set forth as SEQ ID NO:10 and a CDR3 having a sequence set forth as SEQ ID NO:11.

5. The polypeptide of claim 4 which comprises the at least one single domain antibody and at least one other single domain antibody.

6. The polypeptide of claim 4 which is a bispecific polypeptide.

7. The polypeptide of claim 4 wherein the single domain antibody is linked to an immunoglobulin domain or an Fc portion.

8. The polypeptide of claim 4 which comprises i) a first fusion protein wherein a CL constant domain of an antibody is fused by its N-terminal end to a C-terminal end of the single domain antibody and ii) a second fusion protein wherein a CHI constant domain of an antibody is fused by its N-terminal end to a C-terminal end of a single domain antibody directed against an antigen different from EGFR.

9. The polypeptide of claim 4 which comprises i) a first fusion protein wherein a CH1 constant domain of an antibody is fused by its N-terminal end to a C-terminal end of a single domain antibody directed against an activating trigger molecule on an effector cell and ii) a second fusion protein wherein a CL constant domain of an antibody is fused by its N-terminal end to a C-terminal end of the single domain antibody.

10. The polypeptide of claim 4 which is a biparatopic polypeptide.

11. The polypeptide of claim 10 which comprises
   i) a first single domain antibody wherein the CDR1 has a sequence set forth as SEQ ID NO: 1, the CDR2 has a sequence set forth as SEQ ID NO:2 and the CDR3 has a sequence set forth as SEQ ID NO:3 and ii) a second single domain antibody wherein the CDR1 has a sequence set forth as SEQ ID NO:9, the CDR2 has a sequence set forth as SEQ ID NO:10 and the CDR3 has a sequence set forth as SEQ ID NO:11, or
   ii) a first single domain antibody having a sequence set forth as SEQ ID NO:4 and ii) a second single domain antibody having a sequence set forth as SEQ ID NO:12.

12. The polypeptide of claim 10 wherein the first single domain antibody and the second single domain antibody are linked to each other directly or via a linker.

13. The polypeptide of claim 10 which has a sequence selected from the group consisting of SEQ ID NO: 15, SEQ ID NO:13 and SEQ ID NO:14.

* * * * *